(12) United States Patent
Wang

(10) Patent No.: US 9,901,476 B2
(45) Date of Patent: Feb. 27, 2018

(54) EXPANSION BAND WITH UNILATERAL STRAIN AND MANUFACTURING METHOD THEREOF

(71) Applicant: Jiang Wang, Jiangsu (CN)

(72) Inventor: Jiang Wang, Jiangsu (CN)

( * ) Notice: Subject to any disclaimer, the term of this patent is extended or adjusted under 35 U.S.C. 154(b) by 667 days.

(21) Appl. No.: 14/179,527

(22) Filed: Feb. 12, 2014

(65) Prior Publication Data

US 2014/0163681 A1    Jun. 12, 2014

Related U.S. Application Data

(62) Division of application No. 13/065,622, filed on Mar. 24, 2011, now Pat. No. 8,685,193.

(51) Int. Cl.
*A61F 5/02* (2006.01)

(52) U.S. Cl.
CPC ......... *A61F 5/028* (2013.01); *Y10T 29/49826* (2015.01)

(58) Field of Classification Search
CPC .................................. A61F 5/028; A61F 5/026
See application file for complete search history.

(56) References Cited

U.S. PATENT DOCUMENTS

| | | | | |
|---|---|---|---|---|
| 4,682,587 A | * | 7/1987 | Curlee | A61F 5/028 128/DIG. 20 |
| 5,450,858 A | * | 9/1995 | Zablotsky | A61F 5/012 128/876 |
| 8,506,508 B2 | * | 8/2013 | Avitable | A61H 9/0078 156/73.5 |
| 2007/0197943 A1 | * | 8/2007 | Hakonson | A61F 5/012 602/13 |

* cited by examiner

*Primary Examiner* — Tarla Patel
(74) *Attorney, Agent, or Firm* — Raymond Y. Chan; David and Raymond Patent Firm

(57) ABSTRACT

An expansion band includes a first layer, a second layer, a shrinking layer for shrinking the first layer and the second layer, a bond line for sealing the first layer and the second layer to form an inner space therein and dividing the inner space into a plurality of air passages which communicate with each other, and an air nozzle communicate with the air passage. The shrinking layer includes a third layer overlapped on the second layer and a plurality of elastic bands extended between the second and third layers.

20 Claims, 23 Drawing Sheets

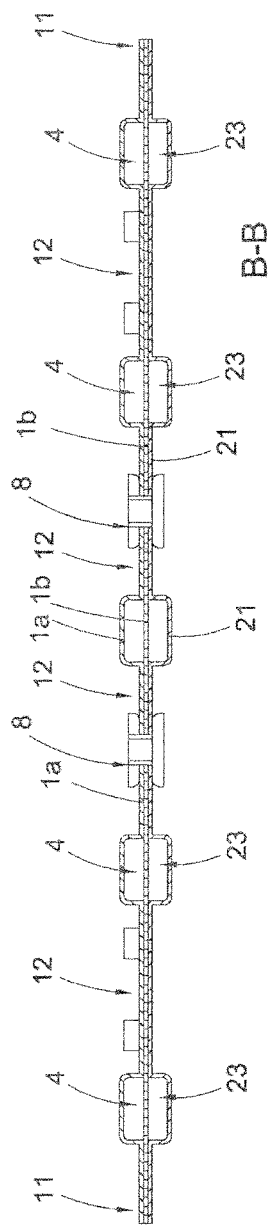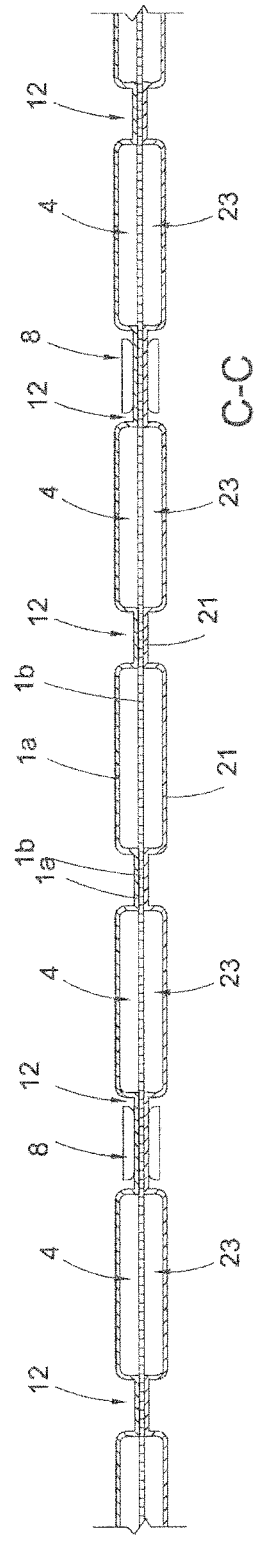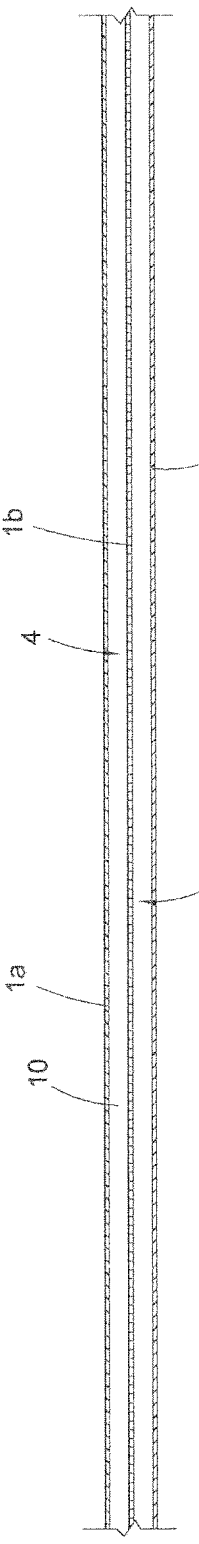

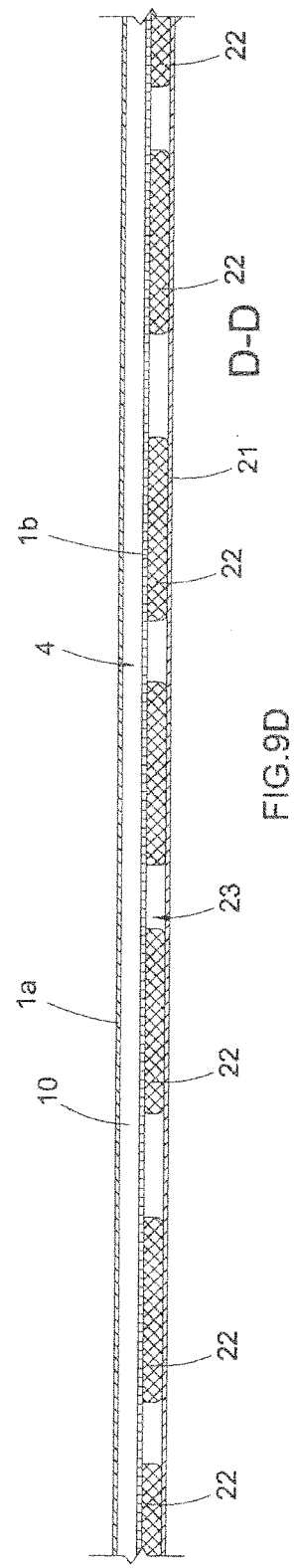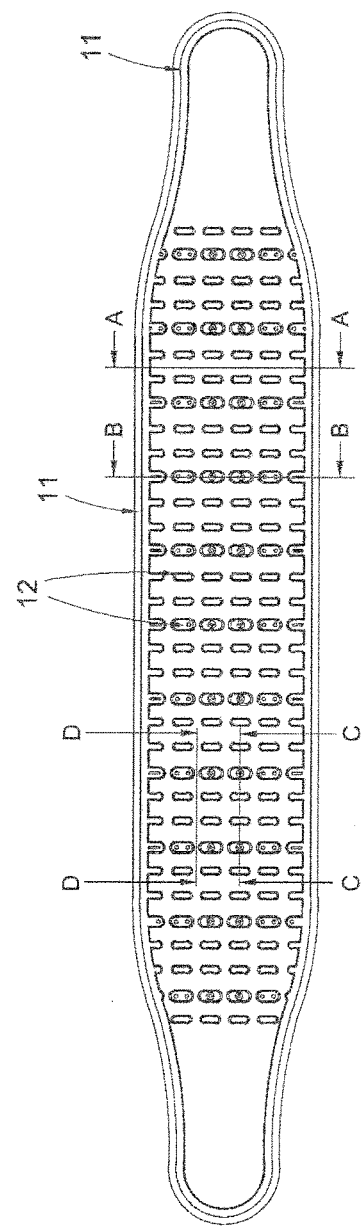

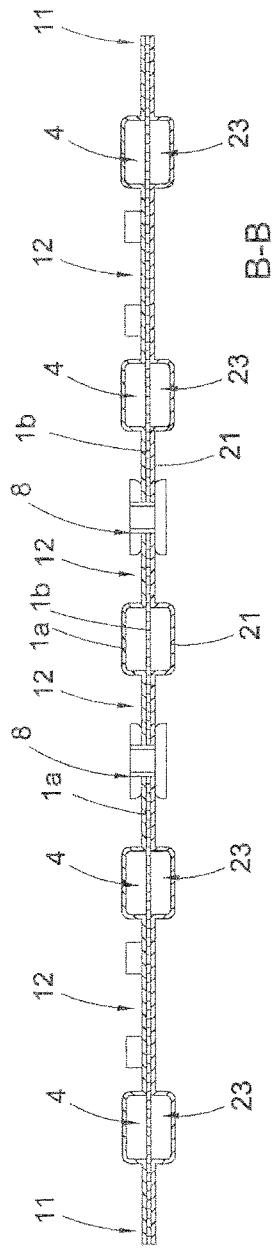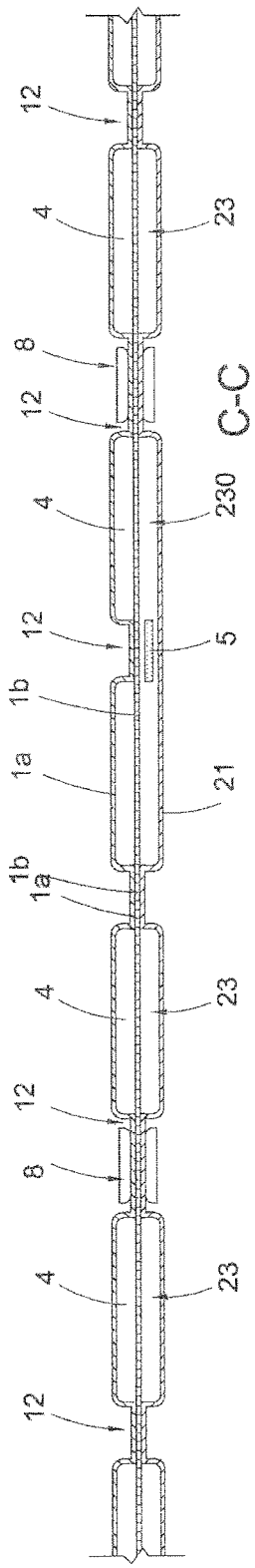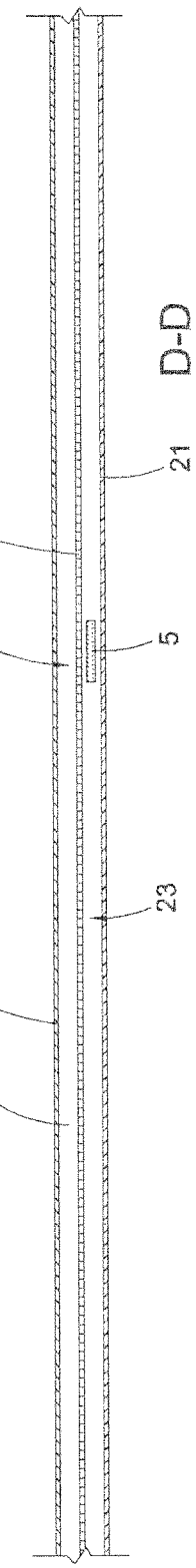

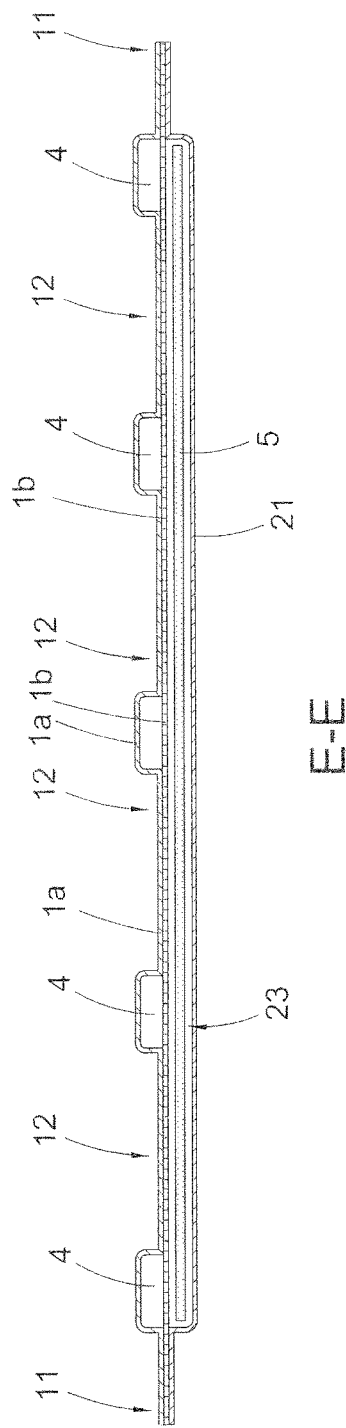
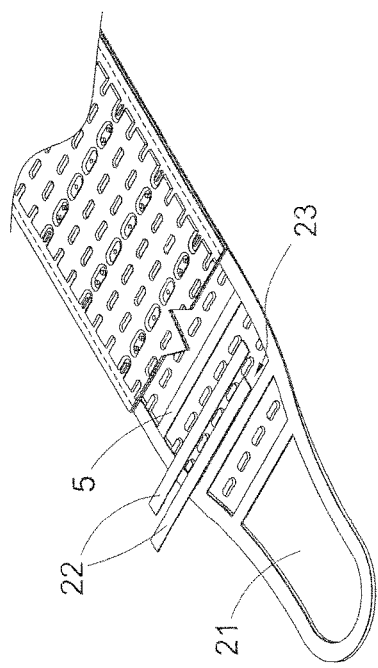

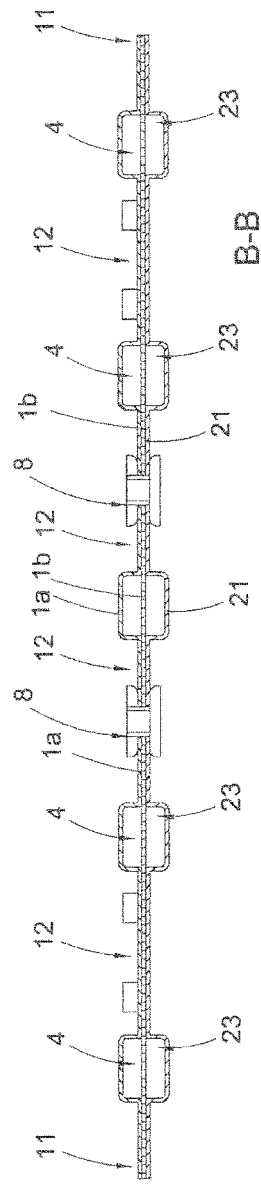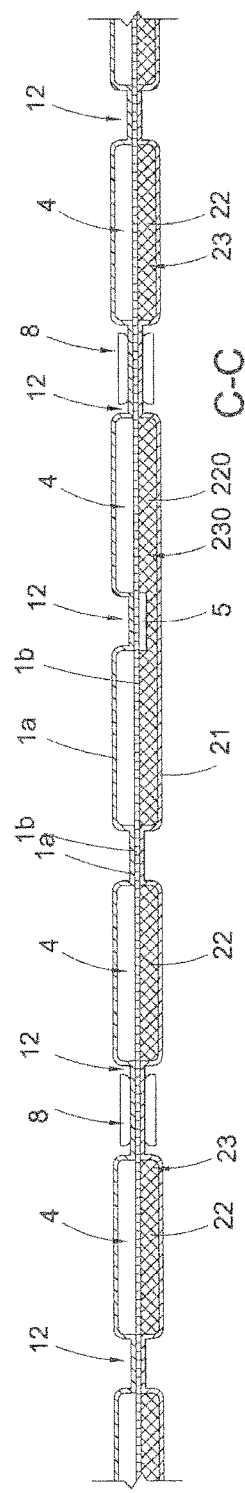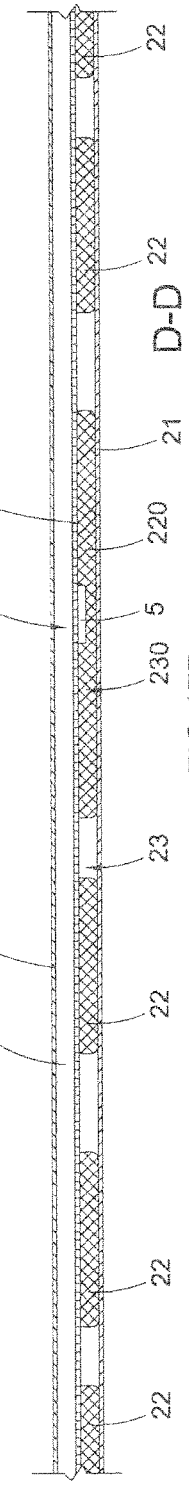

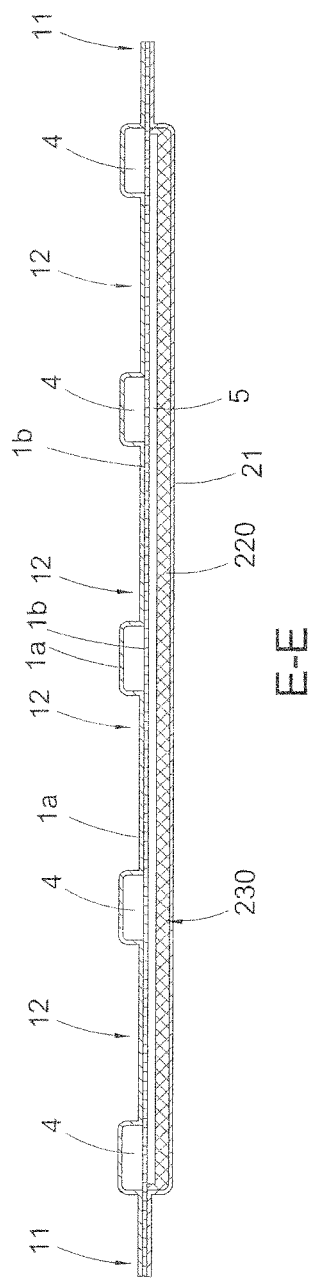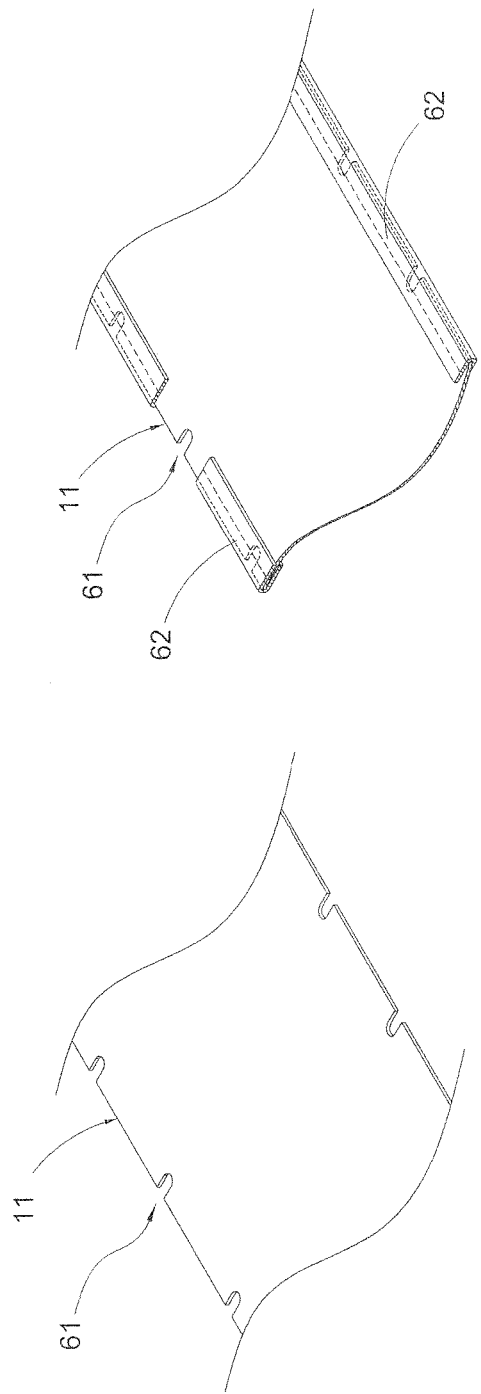

EXPANSION BAND WITH UNILATERAL STRAIN AND MANUFACTURING METHOD THEREOF

CROSS REFERENCE OF RELATED APPLICATION

This is a Divisional application that claims the benefit of priority under 35 U.S.C. § 119 to a non-provisional application, application Ser. No. 13/065,622, filed Mar. 24, 2011.

BACKGROUND OF THE PRESENT INVENTION

1. Field of Invention

The present invention relates to an expansion band, and more particularly to an expansion band with unilateral resistance and a manufacturing method thereof.

2. Description of Related Arts

Generally, an expansion band always has an inner cavity capable of being filled with air or liquid to increase its volume, which causes the expansion of the band. However, this kind of expansion is nondirectional so that this expansion band could not provide a directional expansive force, such as a longitudinal expansive force, which is widely used to force vertebras to stretch to eliminate additional pressure between vertebras.

In U.S. Pat. No. 7,618,509, Ickchun Chang disclosed a wrinkled band as illustrated in FIG. 1A and FIG. 1B. The wrinkled band comprises a first adhesion sheet 01 and a second adhesion sheet 01 overlapped with each other by an outer peripheral rim 01a and an adhesion line 012a, and an elastic band 06 disposed in the inner space 04 of the overlapped adhesion sheets and connected to the above end and the below end of the adhesion sheets 01 by a connection adhesion band 05.

Referring to FIG. 2, the elastic band 06 is stretched by the connection adhesion band 05 and the connection adhesion band 05 is further fixed onto the above below ends of a mounting die 09 to keep the elastic band 06 stretched. The adhesion sheets 01 respectively cover the top bottom surfaces of the mounting die 09 and then are pressed by a high-frequency operating die 08 to form the outer peripheral rim 01a and the adhesion line 012a, thereby the adhesion sheets 01 are overlapped with the elastic band 05 and the connection adhesion band 06 enclosed therein. The outer peripheral rim 01a forms the inner space 04 and the adhesion line 012a further divides the inner space 04 with certain regularity to form an air passage 02. As the elastic band 05 is enclosed in the overlapped adhesion sheets 01, referring to FIG. 1B, the elastic band 05 is enclosed within the air passage formed by the adhesion line 012a.

The high-frequency operating die 08 further comprises a pressurizing means 07 to press the adhesion sheets 01 with the connection adhesion band 06 together. Hence, referring to FIG. 1B, the connection adhesion band 06 is adhered to the adhesion sheets 01 on the outer peripheral rim 01 a to fix the elastic band 05 in the air passage 02, i.e., one end of the elastic band 05 is fixed to an above end of the air passage 02 by a connection adhesion band 06 and another end the elastic band 05 is fixed to an below end the air passage 02 by a connection adhesion band 06.

As mentioned above, the elastic band 05 is disposed within the air passage 02 and is adhered to the overlapped adhesion sheets 01, when the wrinkled band relaxes, the elastic band 05 contracts to a relaxation situation to wrinkle the adhesion sheets 01 together with a smaller longitudinal length, then when air passage 02 is filled with air, the wrinkled band expands with a bigger longitudinal length and stretches the adhered elastic band 05, which further strains the adhesion sheets 01 back. That means the elastic band 05 resists the expansion of the expansion band, and the resistance of the elastic band 05 affects the expansive force on all the laterals of the wrinkled band.

As the elastic band 05 and the adhesion sheets 01 are fixed together only by the outer peripheral rim 01a, when the wrinkled band expands, the outer peripheral rim 01a not only bears the expansive force provided by the air inside, but also bears the strain force provided by the elastic band 05. Then as the outer peripheral rim 01a is formed only by heated and pressed by the high-frequency operating die 08, the outer peripheral rim 01a cannot bear these forces much, persistently and frequently. That means the outer peripheral rim 01a is very easily to be torn up by these forces, resulting that the air will leak out. Finally, the wrinkled band can not be used anymore.

Referring to FIG. 3, a body is surrounded by the wrinkled band, which is subsequently filled with air to expand, the expansive force on the surface touching the body forces the vertebras to stretch, thereby the additional pressure between the vertebras will be eliminated. However, as the elastic band 05 disposed within the air passage 02 strains all the adhesion sheets 01 back in the opposite direction, the strain force will balance a part of the expansive force. Hence, the expansive force of the wrinkled band is decreased by the resistance of the elastic band 5 and cannot be used effectively to obtain a satisfied treatment effect.

Furthermore, considering that the adhesion sheets 01 and the stretched elastic band 05 are pressed together by the high-frequency operating die 08 at the same time, it is very hard to control the pressure. If the pressure is a little smaller, the outer peripheral rim 01a will not be strong enough to bear the strain force of the elastic band 05, then the adhesion sheets 01 will be torn up to cause a waste product. Besides, the high-frequency operating die 08 is always heated to weld the adhesion sheets 01 together, and then the adhesion sheets 01 are cooled to form the outer peripheral rim 01a. However, if the heating time or the cooling time is not controlled well, a waste product will be obtained.

SUMMARY OF THE PRESENT INVENTION

It will be appreciated that the present invention provides an expansion band capable of expanding when filled with air.

It will be appreciated that the present invention provides an expansion band with an inner space and a plurality of air passages formed by bonding a first layer and a second layer in accordance with a pre-determined pattern.

It will be appreciated that the present invention provides an expansion band with an inner space and a plurality of air passages formed by bonding a first layer and a second layer along a bond line.

It will also be appreciated that the present invention provides an expansion band with a shrinking layer for shrinking the expansion band.

It will also be appreciated that the present invention provides an expansion band with enhanced expansive force.

Accordingly, the present invention is directed to an expansion band, which comprises a first layer, a second layer, a shrinking layer for shrinking the first layer and the second layer, a bond line for sealing the first layer and the second layer to form an inner space therein and dividing the inner space into a plurality of air passages communicated with each other, a plurality of air passages formed between the first layer and the second layer, and an air nozzle for communicating with the air passage.

In a preferred embodiment of the present invention, the shrinking layer is bonded to the outline of the second layer.

In a preferred embodiment of the present invention, the shrinking layer comprises a third layer and a plurality of elastic bands attached thereon.

In a preferred embodiment of the present invention, the expansion band comprises a bond line for forming an inner space between the first layer and the second layer, dividing the inner space into a plurality of air passages communicated with each other, and forming a plurality of passages between the second layer and the third layer, a plurality of air passages formed between the first layer and the second layer.

In a preferred embodiment of the present invention, the expansion band comprises a plurality of passages for guiding the elastic band to pass through, wherein the elastic band is disposed between the second layer and the third layer.

In a preferred embodiment of the present invention, the bond line bonds the first layer, the second layer and the third layer together.

In a preferred embodiment of the present invention, the bond line bonds outline and pre-determined regions of the first layer and the second layer together, and the shrinking layer attaches to the second layer to shrink the first layer and the second layer, the plurality of air passages disposed between the first layer and the second layer.

The present invention further provide a method of manufacturing an expansion band, which comprises the steps:

(a) bonding a first layer, a second layer and a third layer of a shrinking layer together to form a bond line, wherein the first layer and the second layer are sealed by the bond line on outline to form an inner space between the first layer and the second layer, the inner space is divided by the bond line into a plurality of air passages;

(b) providing a plurality of elastic bands to extend between the second layer and the third layer, and fixing the elastic bands onto outline of the first layer, the second layer and the third layer.

In a preferred embodiment of the present invention, step (a) further comprises:

pressing the first layer, the second layer and the third layer to a die with pre-determined pattern;

forming the bond line in accordance to the pre-determined pattern of the die to bond the first layer, the second layer, and the third layer together;

wherein the bond line seals outline of the first layer and second layer to form the inner space and bonds regions of the first layer and second layer to divide the inner space into the plurality of air passages capable of communicating with each other.

In a preferred embodiment of the present invention, step (b) further comprises:

guiding the elastic bands to enter the passages;
stretching the elastic bands to pass through the passages;
fixing the elastic bands in stretching state onto the first layer, the second layer and the third layer.

In a preferred embodiment of the present invention, the method further comprises a step (c) of connecting an air nozzle to the air passage.

These and other objectives, features, and advantages of the present invention will become apparent from the following detailed description, the accompanying drawings, and the appended claims.

BRIEF DESCRIPTION OF THE DRAWINGS

FIG. 7B is a B-B section view of the product of FIG. 6B.
FIG. 7C is a C-C section view of the product of FIG. 6B.
FIG. 7D is a D-D section view of the product of FIG. 6B.

FIG. 9D is a D-D section view of the product of FIG. 8B.

FIG. 10B is a perspective view of the product manufactured by the pressing procedure of FIG. 10A.

FIG. 15B is a B-B section view of the product of FIG. 14B.

FIG. 15C is a C-C section view of the product of FIG. 14B.

FIG. 15D is a D-D section view of the product of FIG. 14B.

FIG. 15E is an E-E section view of the product of FIG. 14B.

FIG. 16A is a perspective view illustrating the procedure of providing the elastic means to the product in FIG. 14B.

FIG. 17B is a B-B section view of the product of FIG. 16B.

FIG. 17C is a C-C section view of the product of FIG. 16B.

FIG. 17D is a D-D section view of the product of FIG. 16B.

FIG. 17E is an E-E section view of the product of FIG. 16B.

FIG. 18A is an enlarged partial view of the product manufactured by the pressing procedure illustrating the cut thereon.

FIG. 18B is a perspective view illustrating the sewing procedure of the expansion band according to the above preferred embodiment.

DETAILED DESCRIPTION OF THE PREFERRED EMBODIMENT

Figure 1A:
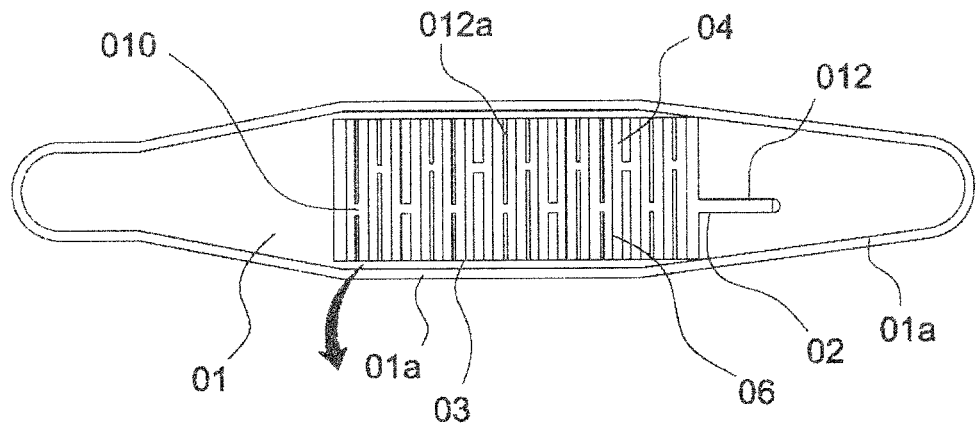
FIG. 1A is a perspective view of a wrinkled band according to the prior art.
Figure 1B:
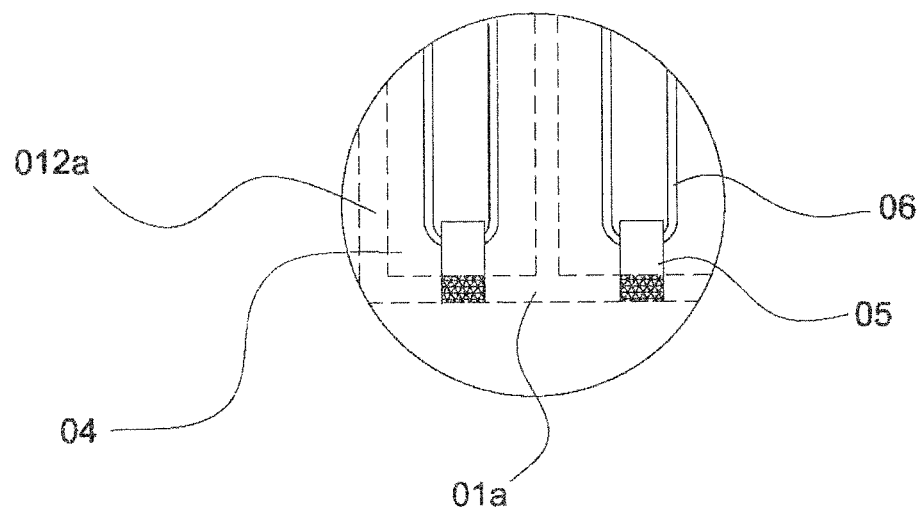
FIG. 1B is an enlarged partial view of the connection adhesion band and the elastic band of FIG. 1A.
Figure 2:
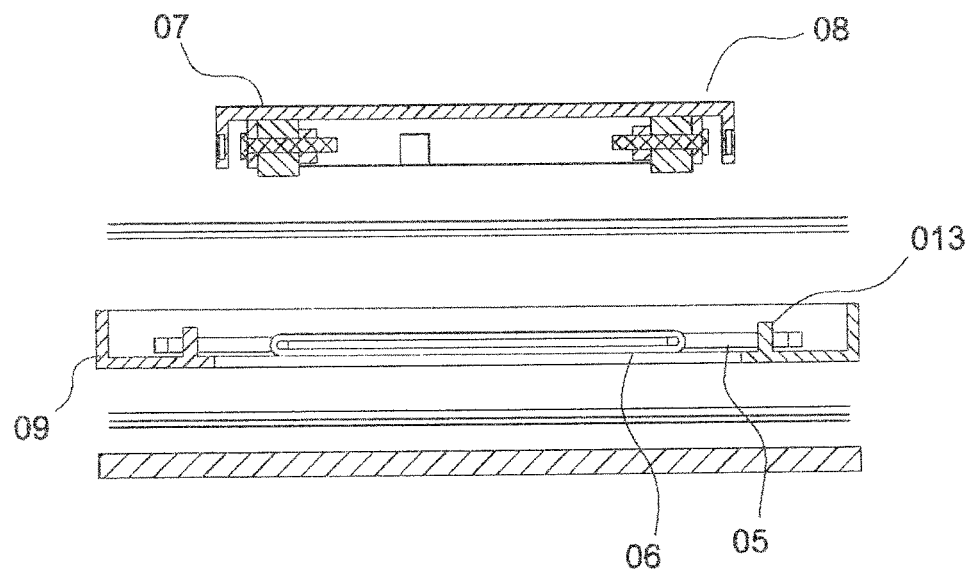
FIG. 2 is a cross-section view showing the procedure of pressing the adhesion sheets, the connection adhesion band and the elastic band by the high-frequency operating die.
Figure 3:
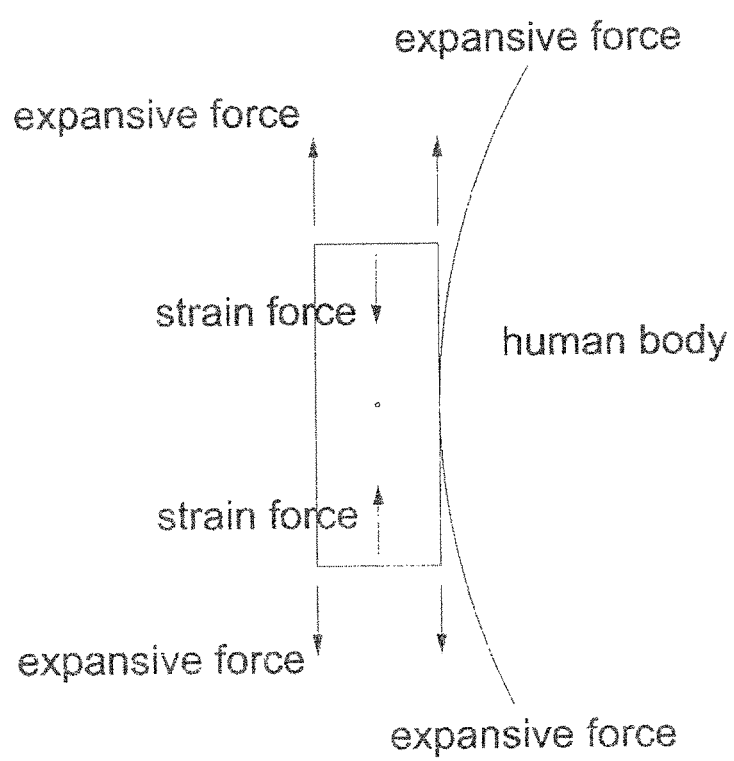
FIG. 3 illustrates the force distribution of the expanded wrinkled band of FIG. 1.
Figure 4:
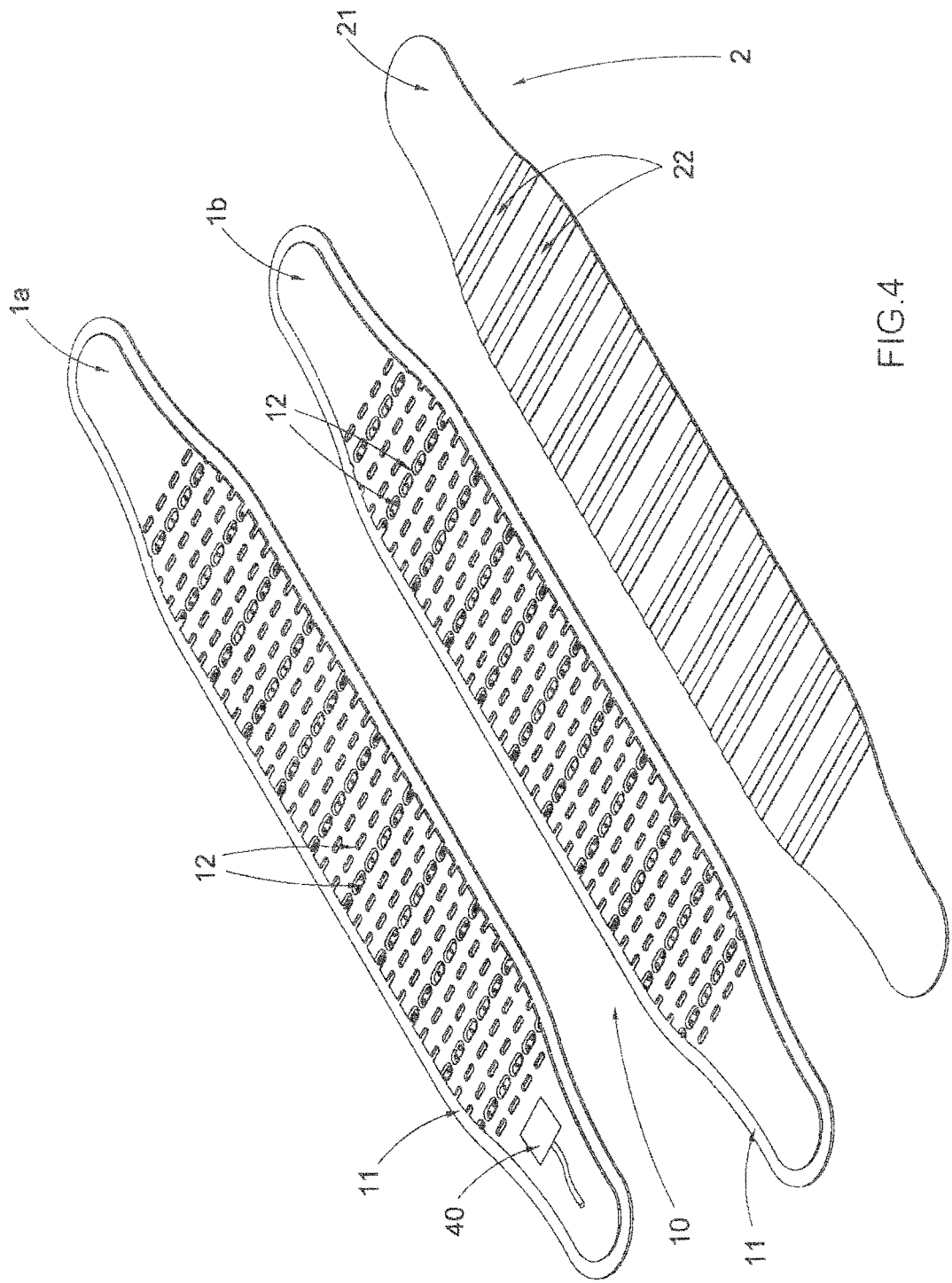
FIG. 4 is an exploded view of an expansion band according to a first preferred embodiment of the present invention.
Figure 5A:
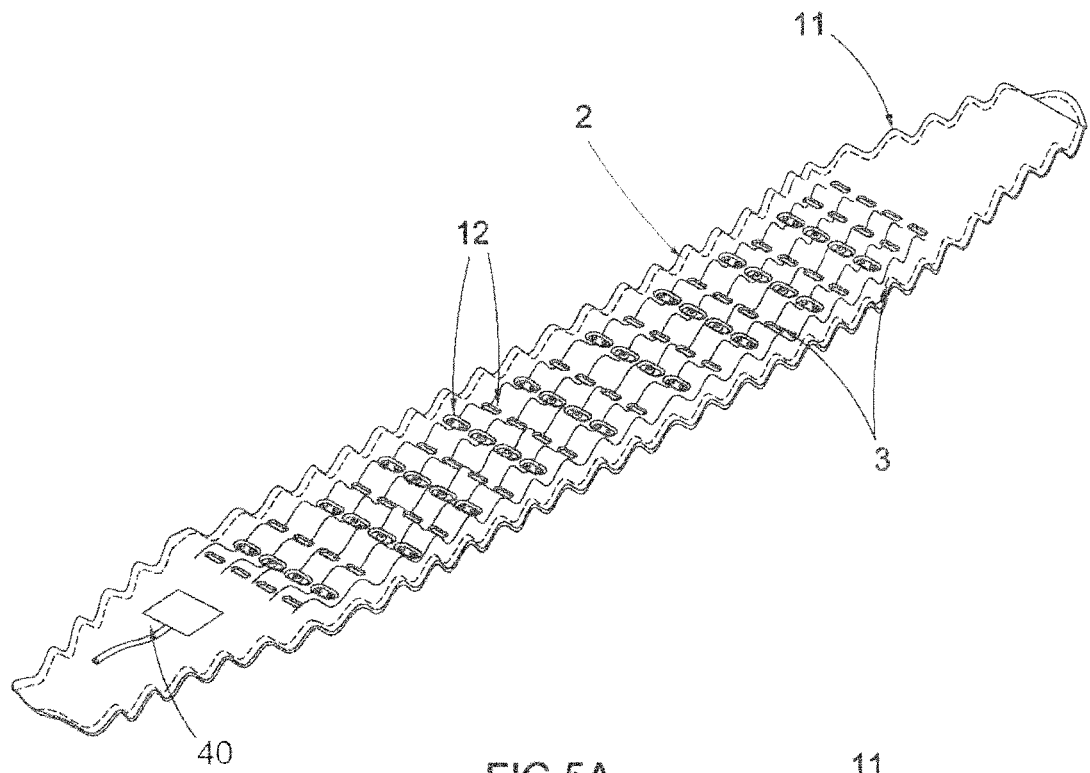
FIG. 5A is a perspective view of the unexpanded expansion band according to the above preferred embodiment of the present invention.
Figure 5B:
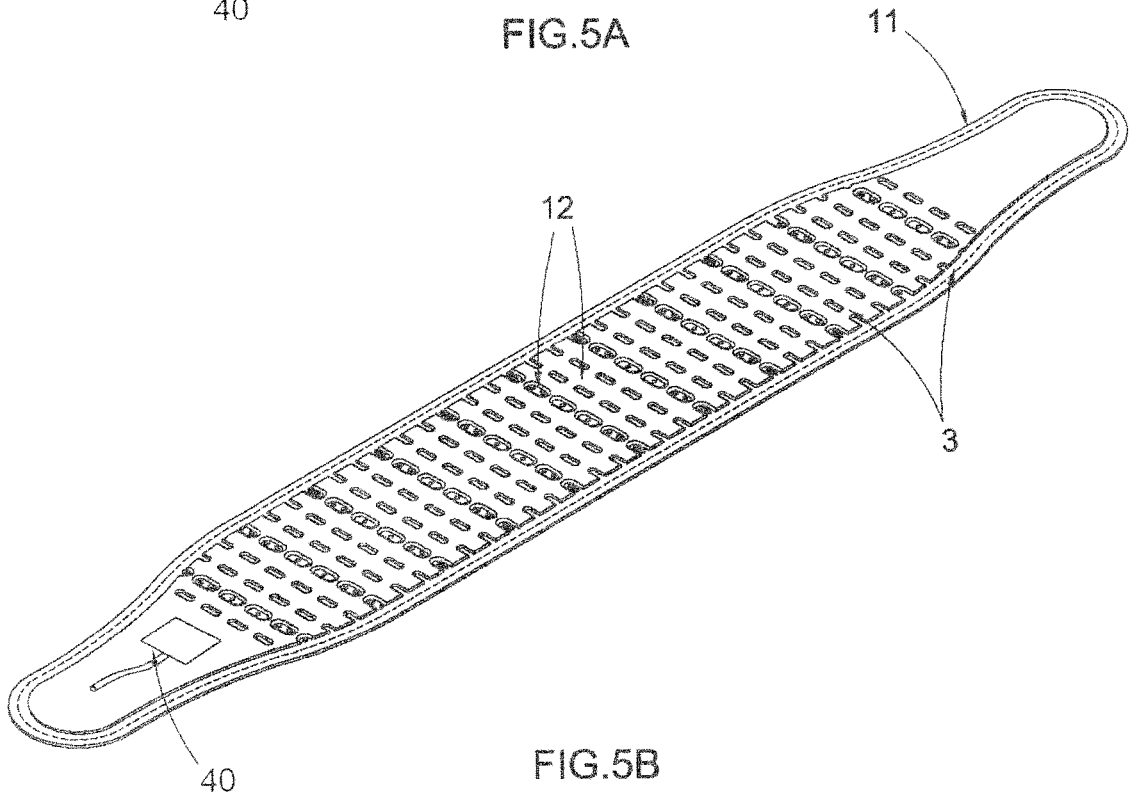
FIG. 5B is a perspective view of the expanded expansion band according to the above preferred embodiment of the present invention.

Referring to FIG. 4, FIG. 5A and FIG. 5B, an expansion band according to a preferred embodiment of the present invention is illustrated. The expansion band comprises a first layer 1a, a second layer 1b, a bond line 3 for sealing the first layer 1a and the second layer 1b to form an inner space 10 therein and dividing the inner space 10 into a plurality of air passages 4, as shown in FIGS. 7A-7D, communicated with each other, a shrinking layer 2 for shrinking the first layer 1a and the second layer 1b, and an air nozzle 40 capable of communicating with the air passage 4.

The first layer 1a and the second layer 1b are pressed to a die 9 having pre-determined pattern, thereby the outlines 11 of the first layer 1a and the second layer 1b are bonded together to form the inner space 10 therein, which is sealed. Furthermore, in accordance to the pre-determined pattern of the die 9, a plurality of regions 12 in the central areas of the first layer 1a and the second layer 1b are bonded together to divide the inner space 10 into the plurality of air passages 4, which are communicated with each other. So not only are the outlines 11 of the first layer 1a and the second layer 1b are adhered, but also some regions 12 are adhered in accordance to the pre-determined pattern; hence the inner space 10 formed between the first layer 1a and the second layer 1b is actually composed of a plurality of line-shape inner spaces, which let the air pass through to form a plurality of air passages 4. The bonded outlines 11 and the bonded regions 12 form the bond line 3, which means the bond line 3 seals the first layer 1a and the second layer 1b to form the inner space 10 and further divide the inner space 10 into the plurality of air passages 4.

The shrinking layer 2 is bonded to the outline 11 of the second layer 1b and is capable of shrinking. Hence, when the expansion band is unexpanded as illustrated in FIG. 5A, the shrinking layer 2 shrinks and further strains the first layer 1a and the second layer 1b to the centre, so that the first layer 1a and the second layer 1b are shrunk and have wrinkles thereon.

Then when the expansion band is filled with air through the air nozzle 40 to expand, the first layer 1a and the second layer 1b are unfolded as illustrated in FIG. 5B. Along the expansion of the expansion band, the unfolded first layer 1a and the second layer 1b are stretching the shrinking layer 2 to extend, and then the shrinking layer 2 will generate a strain force to resist the extension. The strain force of the shrinking layer 2 is increased along the extension and further strains the first layer 1a and the second layer 1b back against the expansion. However, along the expansion of the expansion band, the expansive force is also being increased to gradually balance the strain force. Finally, the expansion band is expanded as illustrated in FIG. 5B, with the shrinking layer 2 stretched.

Then when the air in the expansion band is discharged through the air nozzle 40, the expansive force is decreased along the discharging and cannot balance the strain force of the shrinking layer 2 anymore. As a result, the shrinking layer shrinks and strains the first layer 1a and the second layer 1b to the centre, and finally the expansion band is shrunk as illustrated in FIG. 5A.

In a preferred embodiment of the present invention, the shrinking layer 2 comprises a third layer 21 and a plurality of elastic bands 22 attached thereon, wherein the elastic bands 22 parallel extends on the outer surface of the second layer 1b in the width direction thereof.

In order to shrink the first layer 1a and the second layer 1b, the elastic band 22 is fixed to the outline 11 on two sides of the second layer 1b in a stretching state. That means after the air passages 4 are formed, the elastic bands 22 are respectively stretched to extend on the outer surfaces of the second layer 1b and then two ends of each elastic band 22 are fixed onto the outline 11 on two sides of the second layer 1b.

Hence, when there is no expansive force, the stretched elastic bands 22 will strain the sealed first layer 1a and second layer 1b along the width direction, so that the sealed first layer 1a and second layer 1b are shrunk by the elastic bands 22 and have the width decreased.

In a preferred embodiment of the present invention, the elastic band 22 extends along the outer surface of the air passage 4. And at least one elastic band 22 extends along the bond line 3.

Figure 6A:
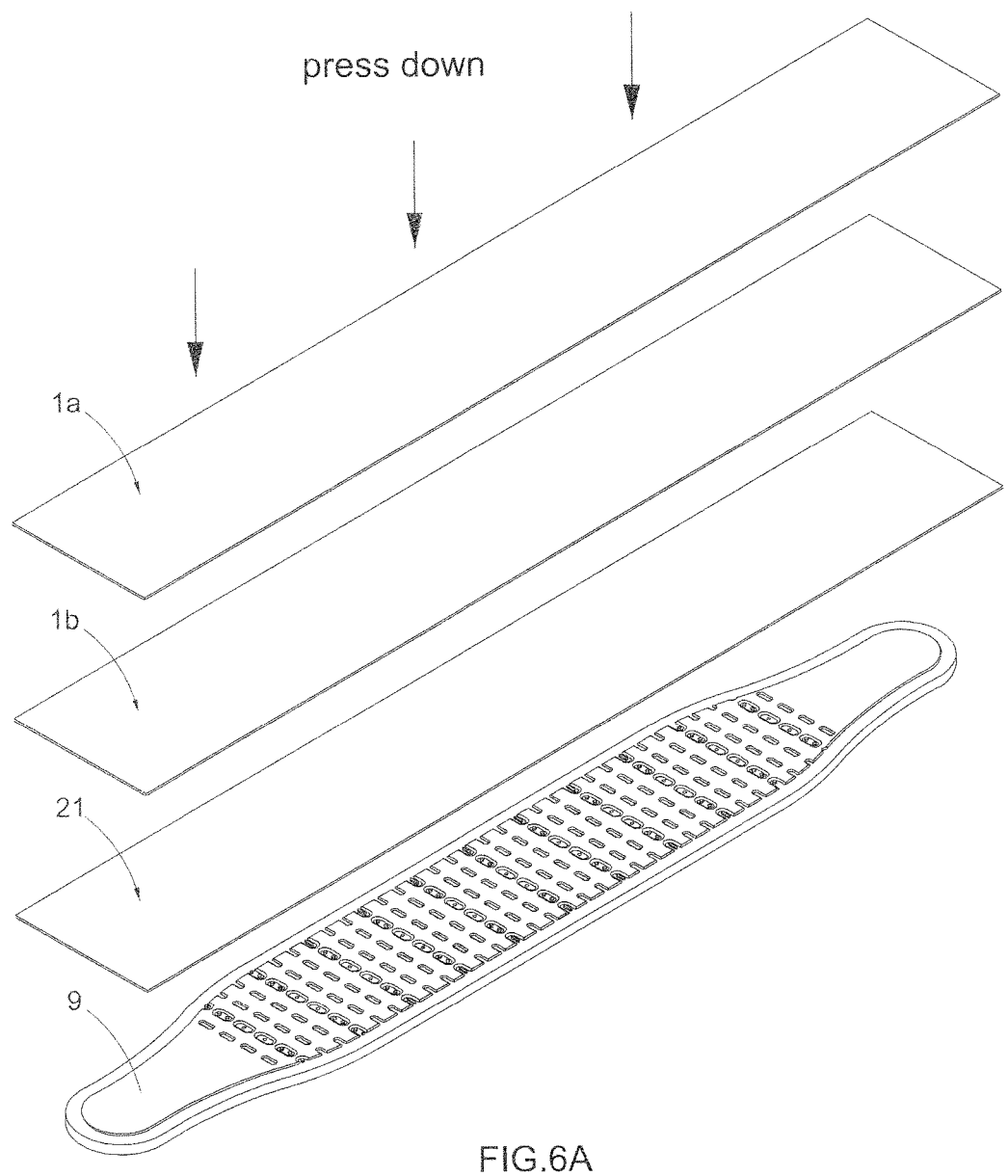
FIG. 6A is a perspective view illustrating the pressing procedure according to the above preferred embodiment of the present invention.

In a preferred embodiment of the present invention, the first layer 1a, the second layer 1b and the shrinking layer 2 are bonded together as illustrated in FIG. 6A.

The third layer 21 of the shrinking layer 2, the second layer 1b and the first layer 1a are provided onto the die 9 in turn, wherein the die 9 has pre-determined pattern disposed thereon. Then the first layer 1a, the second layer 1b and the third layer 21 are pressed down to the die 9 with a pre-determined pressure. It is preferred that the die 9 has already been heated to a pre-determined temperature to heat the third layer 21, the second layer 1b and the first layer 1a provided thereon. Due to the press and/or the heat, the bond line 3 is formed in accordance to the pre-determined pattern of the die 9 to bond the first layer 1a, the second layer 1b and the third layer 21 together.

As mentioned above, the bond line 3 bonds the outline 11 of the first layer 1a and second layer 1b to seal them and to form the inner space 10 therein, and bonds some regions 12 of the first layer 1a and second layer 1b to divide the inner space 10 into the plurality of air passages 4 communicated with each other. It is preferred that the third layer 21 is also bonded to the second layer 1b by the bond line 3.

Figure 6B:
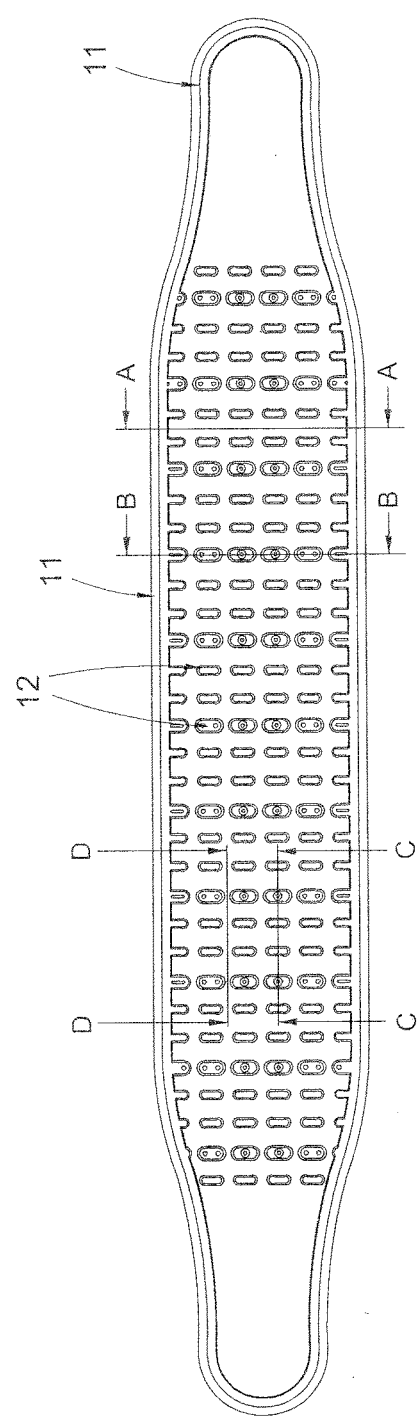
FIG. 6B is a perspective view of the product manufactured by the pressing procedure of FIG. 6A.

Referring to FIG. 6B, the first layer 1a, the second layer 1b and the third layer 21 are bonded together on the positions of the bonded regions 12, so that the air passages 4 are generated in the inner space 11 between the first layer 1a and the second layer 1b while a plurality of passages 23 are also generated between the second layer 1b and the third layer 21 for guiding the elastic bands 22 to drill through.

Figure 7A:
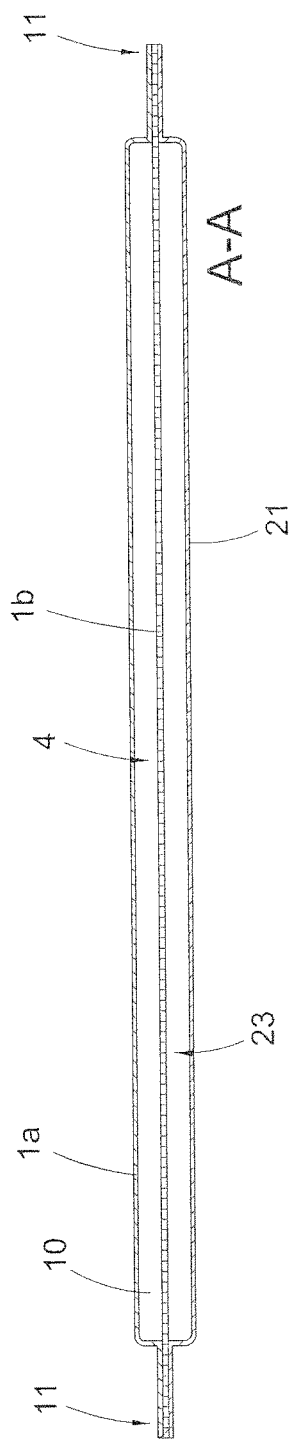
FIG. 7A is an A-A section view of the product of FIG. 6B.

Referring to FIG. 7A, the first layer 1a and the second layer 1b are bonded together on the outline 11 to form the inner space 10. An air passage 4 is generated in the inner space 10, while a passage 23 is generated between the second layer 1b and the third layer 21 to let the elastic band 22 pass through.

Referring to FIG. 7B, the first layer 1a, the second layer 1b and the third layer are bonded together not only on the outline 11, but also on the regions 12. The air passages 4 are generated in the inner space 10 formed between the first layer 1a and the second layer 1b.

Referring to FIG. 7C, the first layer 1a, the second layer 1b and the third layer 21 are bonded together on the regions 12 to form the air passages 4 in the inner space 10 between the first layer 1a and the second layer 1b and to form the passages 23 between the second layer 1b and the third layer 21 to let the elastic bands 22 pass through.

Referring to FIG. 7D, some portions of the first layer 1a, the second layer 1b and the third layer 21 are not bonded together. Hence, the inner space 10 between the first layer 1a and the second layer 1b forms an air passage 4 here, which is communicates with the air passages 4 shown in FIGS. 7A and 7B.

Figure 8A:
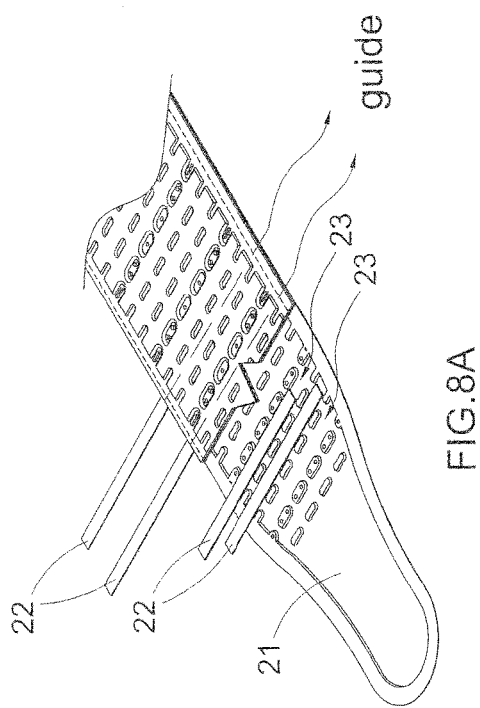
FIG. 8A is a perspective view illustrating the procedure of providing the elastic means to the product in FIG. 6B.

The elastic band 22 is guided to pass through the passage 23 formed between the second layer 1b and the third layer 2 as illustrated in FIG. 8A. As mentioned above, the elastic band 22 is in a stretching state in the passage 23. That means, the elastic band 22 is guided to enter the passage 23 and stretched to pass through the passage 23.

It is preferred that one end of the elastic band 22 is fixed onto an external frame 91, then another end of the elastic band 22 is guided to enter the passage 23 and is stretched to pass through the passage 23 and is fixed onto another external frame 92.

Hence, the elastic band 22 keeps the stretching state in the passage 12 when and after being guided to pass through the passage 23.

Referring to FIG. 18B, when the required elastic bands 22 are all passed through the passages 23, stretched elastic bands 22 are fixed with the first layer 1a, the second to layer 1b and the third layer 21 on the outline 11. Better still, the first layer 1a, the second layer 1b and the third layer 21 are sewn together alone the outline 11, thereby the elastic bands 22 are also sewn with the first layer 1a, the second layer 1b and the third layer 21. That causes the elastic bands 22 are in stretching state when being fixed or sewed to the first layer 1a, the second layer 1b and the third layer 21. Hence, the elastic bands 22 will shrink to strain the first layer 1a, the second layer 1b and the third layer 21 back as illustrated in FIG. 5A.

Figure 8B:
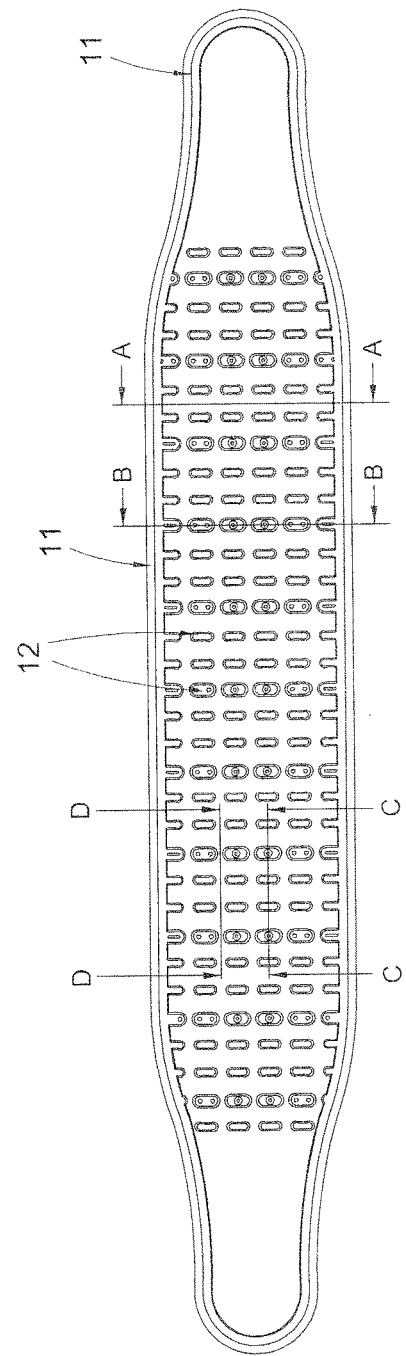
FIG. 8B is a perspective view illustrating the product manufactured by the procedure of FIG. 8A.

Referring to FIG. 8B, the elastic band 22 is stretched and guided to extend on the outer surface of the second layer 1b and to pass through the passage 23 formed between the second layer 1b and the third layer 21.

Figure 9A:
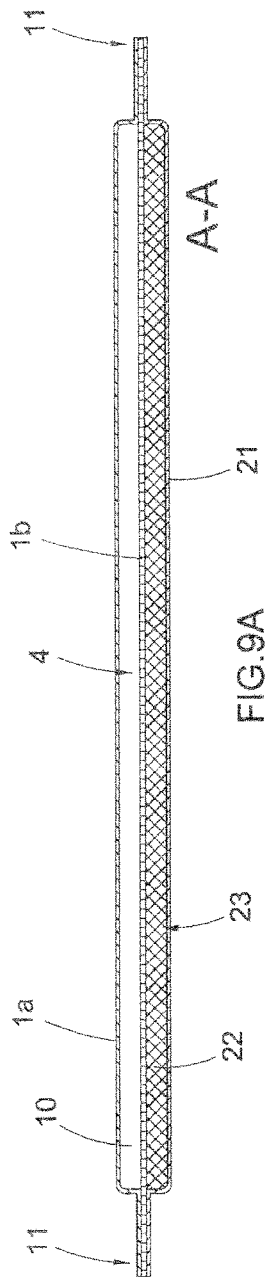
FIG. 9A is an A-A section view of the product of FIG. 8B.

Referring to FIG. 9A, an elastic band 22 has been guided to pass through the passage 23 formed between the second layer 1b and the third layer 21. The elastic band 22 is disposed on the outer surface of the second layer 1b and on the air passage 4 formed between the first layer 1a and the second layer 1b.

Figure 9B:
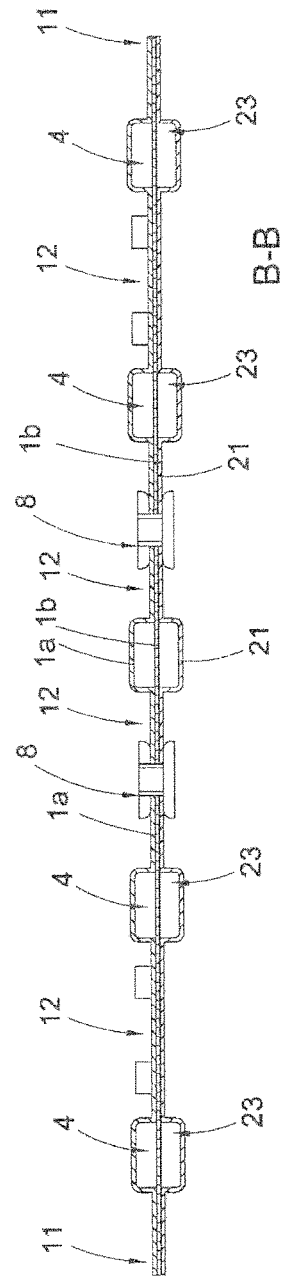
FIG. 9B is a B-B section view of the product of FIG. 8B.

Referring to FIG. 9B, as the first layer 1a, the second layer 1b and the third layer are bonded together not only on the outline 11, but also on the regions 12, only the air passages 4 are formed, while no passage 23 is formed between the second layer 1b and the third layer 21. Hence, no elastic band 22 is disposed here.

Figure 9C:
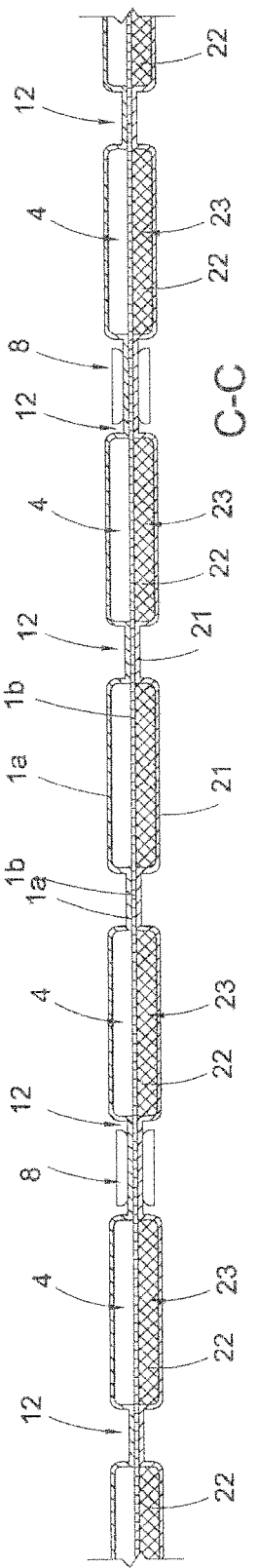
FIG. 9C is a C-C section view of the product of FIG. 8B.

Referring to FIG. 9C and FIG. 9D, as the first layer 1a, the second layer 1b and the third layer 21 are bonded together on the regions 12, not only air passages 4 are formed in the inner space 10 between the first layer 1a and the second layer 1b, but also the passages 23 are formed between the second layer 1b and the third layer 21. Hence, the elastic bands 22 can be guided to pass through these passages 23 in the stretching state. These elastic bands 22 are disposed on the outer surface of the second layer 1b and on the air passages 4.

Figure 10A:
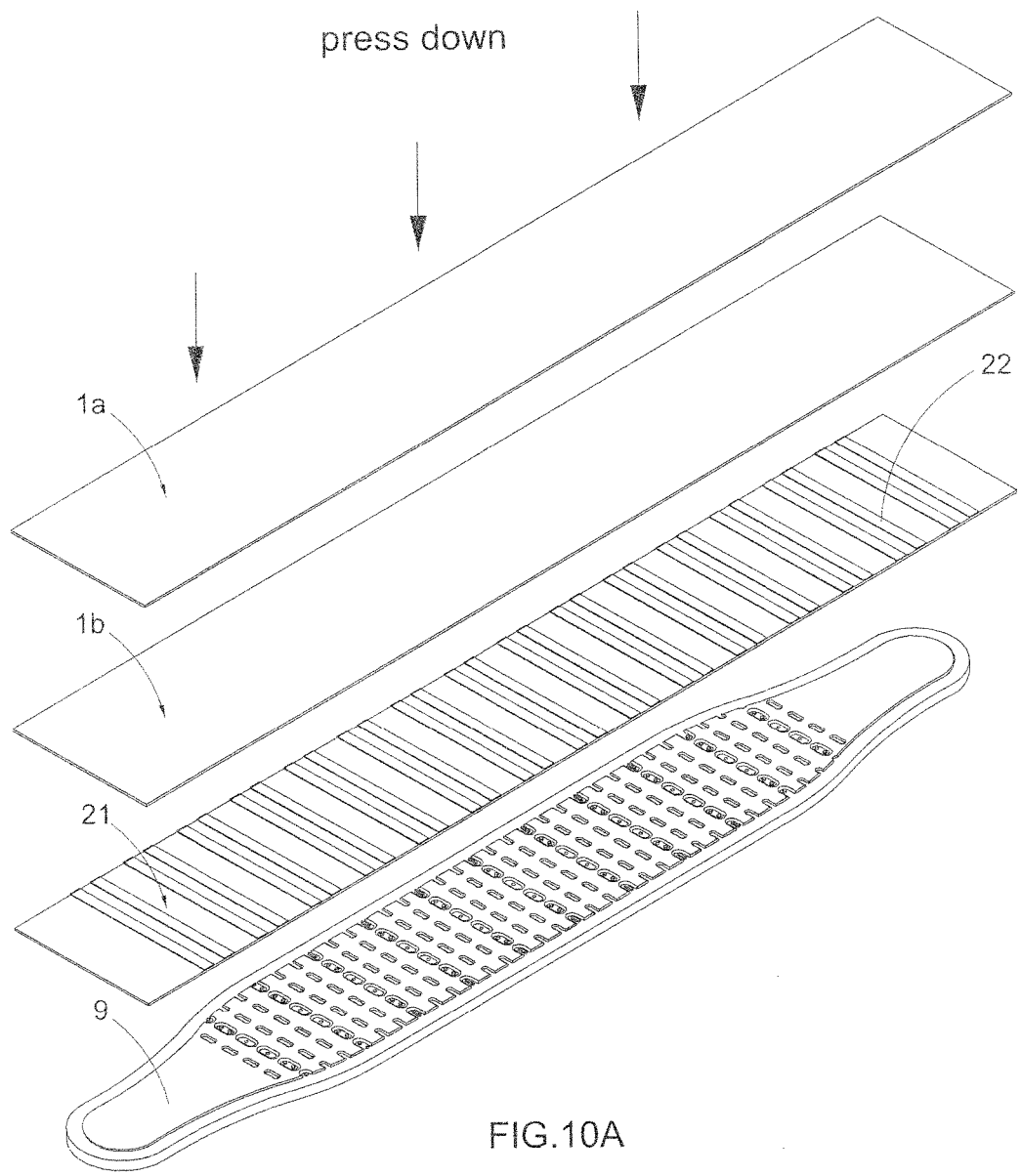
FIG. 10A is a perspective view illustrating the pressing procedure according to another preferred embodiment of the present invention.

In another preferred embodiment of the present invention, a first plurality of elastic bands 21 are pre-provided on the third layer 21 of the shrinking layer 2, which is bonded together with the first layer 1a and the second layer 1b as illustrated in FIG. 10A.

The first plurality of elastic bands 22 could be adhered to the third layer 21 before the pressing procedure, or could be bonded to, be sewn to or be fixed to the third layer 21 by any other suitable method before the pressing procedure. Furthermore, these elastic bands 22 are fixed to the third layer 21 in stretching state, which means these elastic bands 22 are stretched to extend along the wide direction of the third layer 21 and then are fixed onto the corresponding positions of the outline of the third layer 21.

As illustrated in FIG. 10A and FIG. 10B, the third layer 21 of the shrinking layer 2, the second layer 1b and the first layer 1a are provided onto the die 9 in turn, wherein the die 9 has pre-determined pattern disposed thereon, and wherein the first plurality of elastic bands 22 pre-provided on the third layer 21 are disposed between the second layer 1b and the third layer 21.

Then the first layer 1a, the second layer 1b and the third layer 21 are pressed down to die 9 with a pre-determined pressure. As mentioned above, it is preferred that the die 9 has been pre-heated to a pre-determined temperature to heat the third layer 21, the second layer 1b and the first layer 1a provided thereon. Due to the press and/or the heat, the bond line 3 is formed in accordance to the pre-determined pattern of the die 9 to bond the first layer 1a, the second layer 1b and the third layer 21 together.

Better still, the first plurality of elastic bands 22 are arranged in such a manner that the elastic bands 22 are bonded to the second layer 1b by the bond line 3 on parts of the regions 12 in the pressing procedure. As illustrated in FIG. 10B, two air passages 4 are separated by the bond line 3 on the nearby regions 12, which has no elastic band 22 disposed thereon in the pressing procedure as illustrated in FIGS. 6A and 6B, but has an elastic band 22 crossing the third layer 21 fixed or bonded thereon in the pressing procedure as illustrated in FIGS. 10A and 10B.

Therefore, before the pressing procedure, the first plurality of elastic bands 22 are provided in stretching state onto the third layer 21 on the pre-determined positions as mentioned above, and then are bonded together with the first layer 1a, the second layer 1b and the third layer 21 by the bond line 3. Hence, the first plurality of elastic bands 22 extend on the outer surface of the air passages 4 and part of the bond line 3 to cross the width of the third layer 21.

Figure 11A:
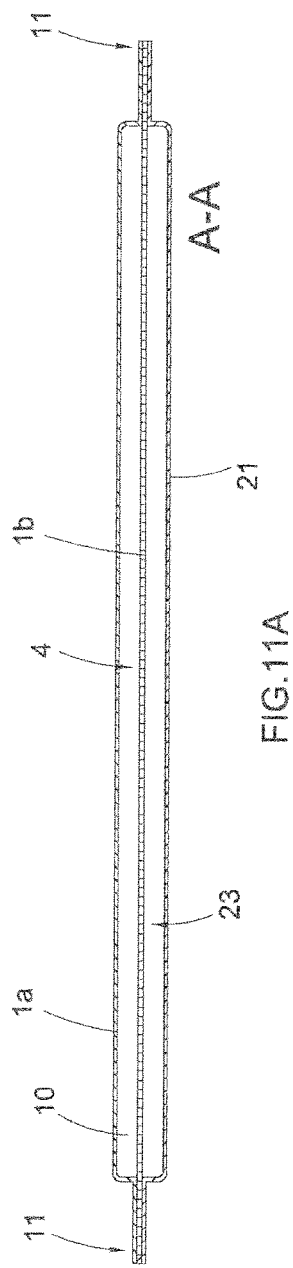
FIG. 11A is an A-A section view of the product of FIG. 10B.

Referring to FIG. 11A, the first layer 1*a* and the second layer 1*b* are bonded together on the outline 11 to form the inner space 10. An air passage 4 is generated in the inner space 10, while a passage 23 is generated between the second layer 1*b* and the third layer 21 to let the elastic band 22 pass through.

Figure 11B:
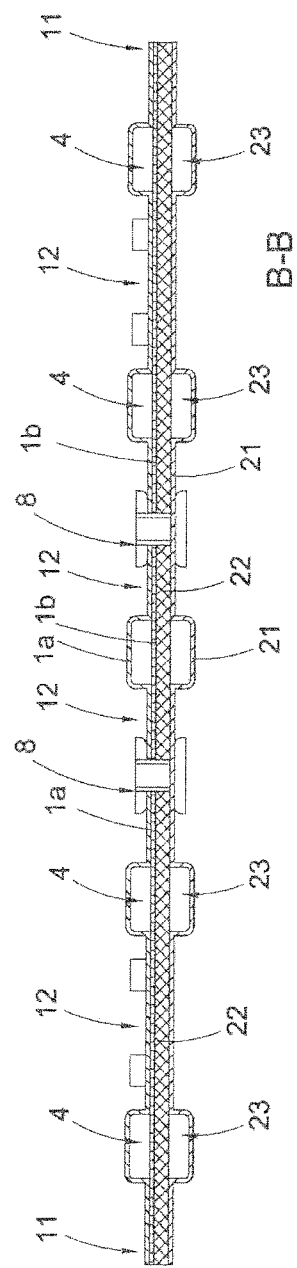
FIG. 11B is a B-B section view of the product of FIG. 10B.

Referring to FIG. 11B, the first layer 1*a*, the second layer 1*b* and the third layer 21 are bonded together not only on the outline 11, but also on the regions 12, wherein an elastic band 22 of the first plurality of elastic bands 22 are disposed between the second layer 1*b* and the third layer 21 and are bonded with the first layer 1*a*, the second layer 1*b* and the third layer 21 on the regions 12. The air passages 4 are generated in the inner space 10 formed between the first layer 1*a* and the second layer 1*b*.

Figure 11C:
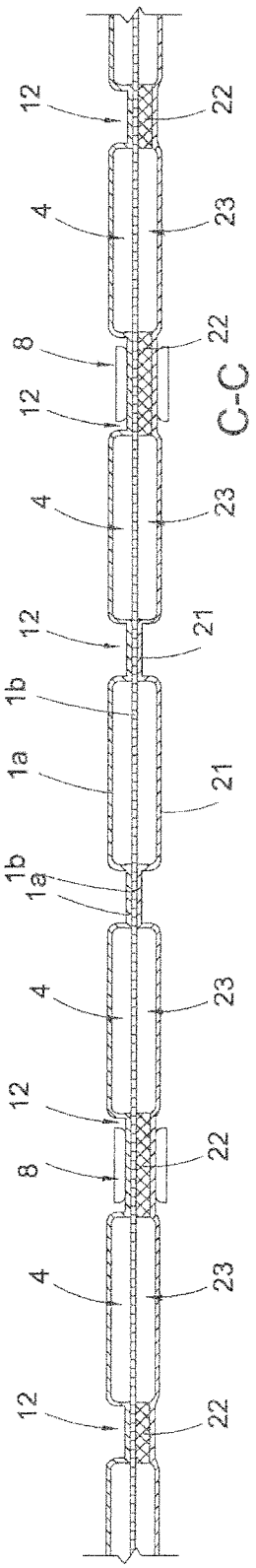
FIG. 11C is a C-C section view of the product of FIG. 10B.

Referring to FIG. 11C, the first layer 1*a*, the second layer 1*b*, the third layer 21 and the first plurality of elastic bands 22 are bonded together on the regions 12, resulting that the air passages 4 in the inner space 10 are formed between the first layer 1*a* and the second layer 1*b*, and the passages 23 are formed between the second layer 1*b* and the third layer 21 to let the second plurality of elastic bands 22 pass through.

Figure 11D:
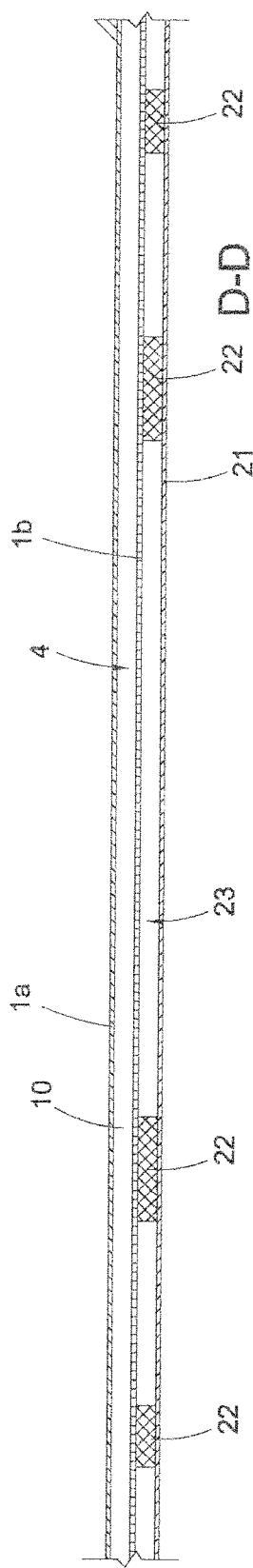
FIG. 11D is a D-D section view of the product of FIG. 10B.

Referring to FIG. 11D, some portions of the first layer 1*a*, the second layer 1*b* and the third layer 21 are not bonded together. Hence, the inner space 10 between the first layer 1*a* and the second layer 1*b* forms an air passage 4 here, which is communicated with the air passages 4 shown in FIGS. 11A and 11B. And the first plurality of elastic bands 22 are disposed on the outer surface of this air passage 4 without being bonded to the second layer 1*b* and the third layer 21. Hence, these no-bonded portions of the first plurality of elastic bands 22 will strain to provide the strain force and further shrink the first layer 1*a* and the second layer 1*b* nearby.

The elastic bands 22 pre-provided on the third layer 21 are better coupled with the first layer 1*a* and the second layer 1*b* than those in FIGS. 6A and 6B, hence, the elastic bands 22 pre-provided on the third layer 21 will better shrink the first layer 1*a* and the second layer 1*b* and more easily form the wrinkles thereon. However, as the elastic bands 22 pre-provided on the third layer 21 are partly fixed to the second layer 1*b* on the regions 12, they cannot provide strain forces as large as those in FIGS. 6A and 6B.

In order to provide enough strain forces to expansion band by the shrinking layer 2, it is preferred that a second plurality of elastic bands 22 are guided to drill through the passages 23 formed between the second layer 1*b* and the third layer 21 by the bond line 3.

Figure 12A:
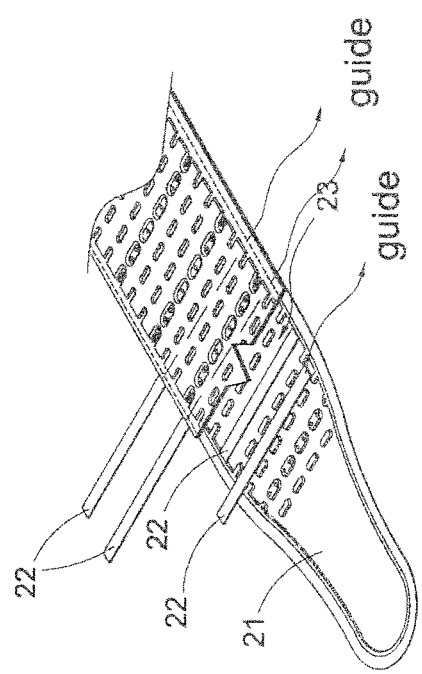
FIG. 12A is a perspective view illustrating the procedure of providing the elastic means to the product in FIG. 10B.

The elastic band 22 of the second plurality of elastic band 22 is guided to pass through the passage 23 formed between the second layer 1*b* and the third layer 2 as illustrated in FIG. 12A. As mentioned above, the elastic band 22 is in a stretching state in the passage 23. That means, the elastic band 22 is guided to enter the passage 23 and is stretched to pass through the passage 23. As mentioned above, one end of the elastic band 22 is fixed onto an external frame 91, and then another end of the elastic band 22 is guided to enter the passage 23 and is stretched to pass through the passage 23 and is fixed onto another external frame 92. Theses stretched elastic bands 22 are fixed with the first layer 1*a*, the second layer 1*b* and the third layer 21 on the outline 11 as mentioned above.

Figure 12B:
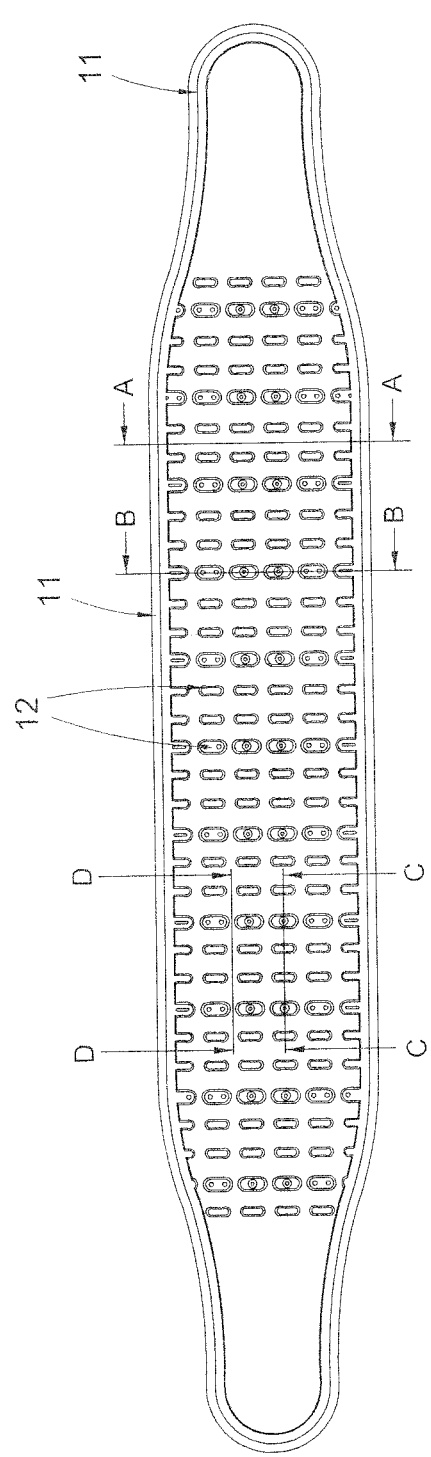
FIG. 12B is a perspective view illustrating the product manufactured by the procedure of FIG. 12A.

Referring to FIG. 12B, while the first plurality of elastic bands 22 have already been disposed between the second layer 1*b* and the third layer 21, each elastic band 22 of the second plurality of elastic bands 22 is stretched and guided to extend on the outer surface of the second layer 1*b* and to pass through the passage 23 formed between the second layer 1*b* and the third layer 21.

Figure 13A:
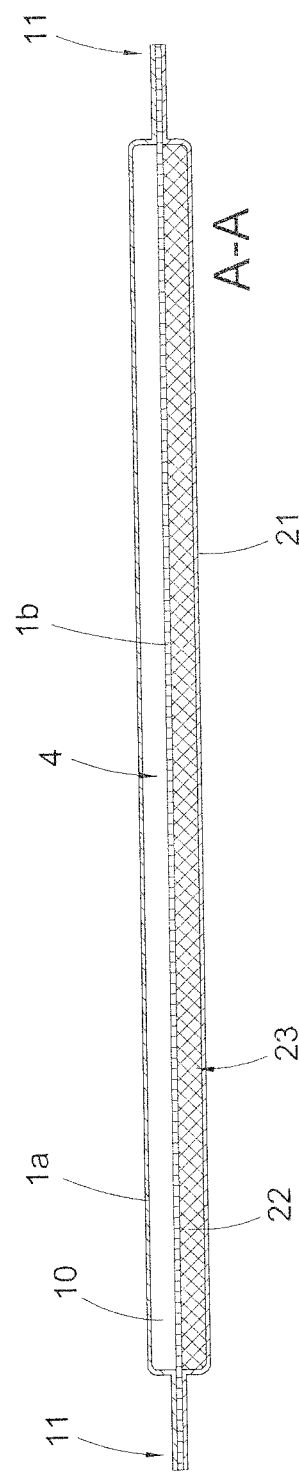
FIG. 13A is an A-A section view of the product of FIG. 12B.

Referring to FIG. 13A, an elastic band 22 has been guided to pass through the passage 23 formed between the second layer 1*b* and the third layer 21. The elastic band 22 is disposed on the outer surface of the second layer 1*b* and on the air passage 4 formed between the first layer 1*a* and the second layer 1*b*.

Figure 13B:
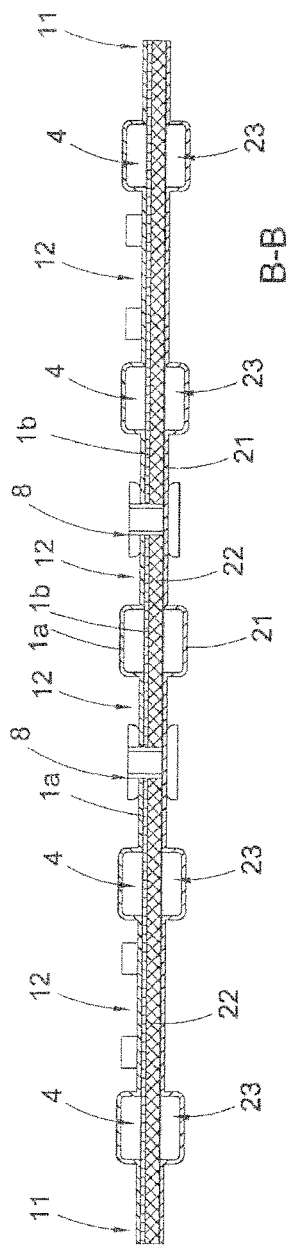
FIG. 13B is a B-B section view of the product of FIG. 12B.

Referring to FIG. 13B, as the first layer 1*a*, the second layer 1*b* and the third layer are bonded together not only on the outline 11, but also on the regions 12, Referring to FIG. 13B, an elastic band 22 of the first plurality of elastic bands 22 are disposed between the second layer 1*b* and the third layer 21 and are bonded with the first layer 1*a*, the second layer 1*b* and the third layer 21 on the regions 12. Hence, only the air passages 4 are formed, while no passage 23 is framed between the second layer 1*b* and the third layer 21, so that, no elastic band 22 of the second plurality of elastic bands 22 is disposed here.

Figure 13C:
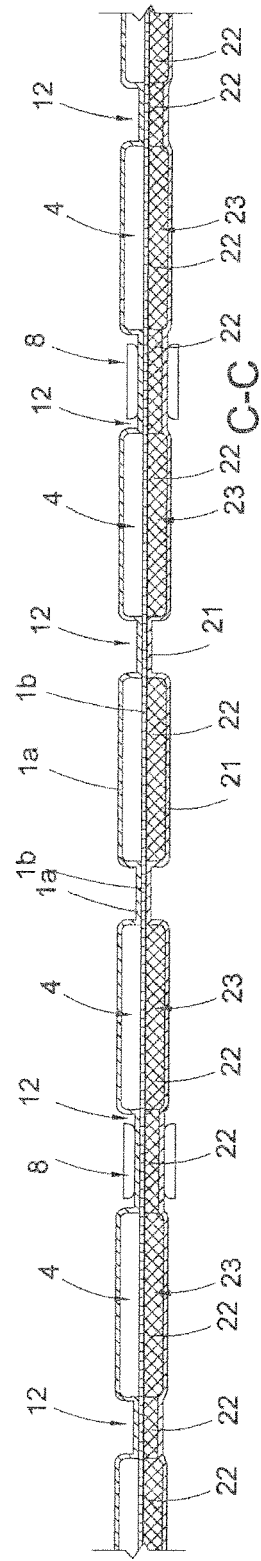
FIG. 13C is a C-C section view of the product of FIG. 12B.
Figure 13D:
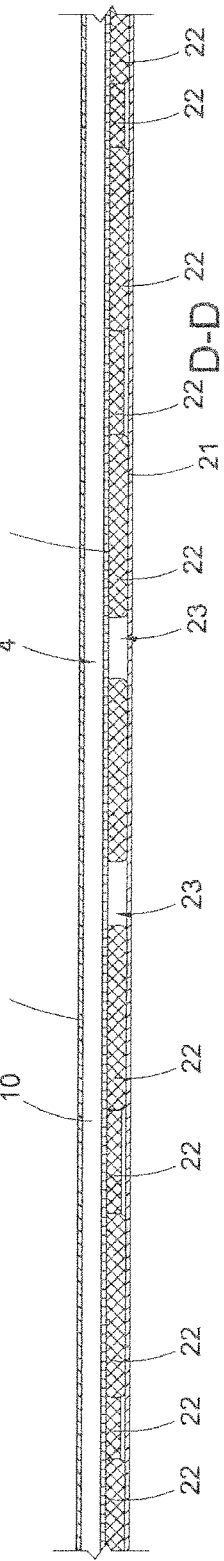
FIG. 13D is a D-D section view of the product of FIG. 12B.

Referring to FIG. 13C and FIG. 13D, as the first layer 1*a*, the second layer 1*b* and the third layer 21 are bonded together on the regions 12, not only air passages 4 are formed in the inner space 10 between the first layer 1*a* and the second layer 1*b*, but also the passages 23 are formed between the second layer 1*b* and the third layer 21. Hence, the second plurality of elastic bands 22 can be guided to pass through these passages 23 in the stretching state and disposed on the outer surface of the second layer 1*b* and on the air passages 4. As the first plurality of elastic bands 21 have already been disposed between the second layer 1*b* and the third layer 21, hence the first plurality and the second plurality of elastic bands 22 both exist in the expansion band.

In this embodiment, with the effect of the first and the second plurality of elastic bands 22, the shrinking layer 2 could provide various strain forces to better shrink the expansion band. With various arrangements of the first and the second pluralities of elastic bands 22, the expansion band could be manufactured with different strain force according to the requirement.

Figure 14A:
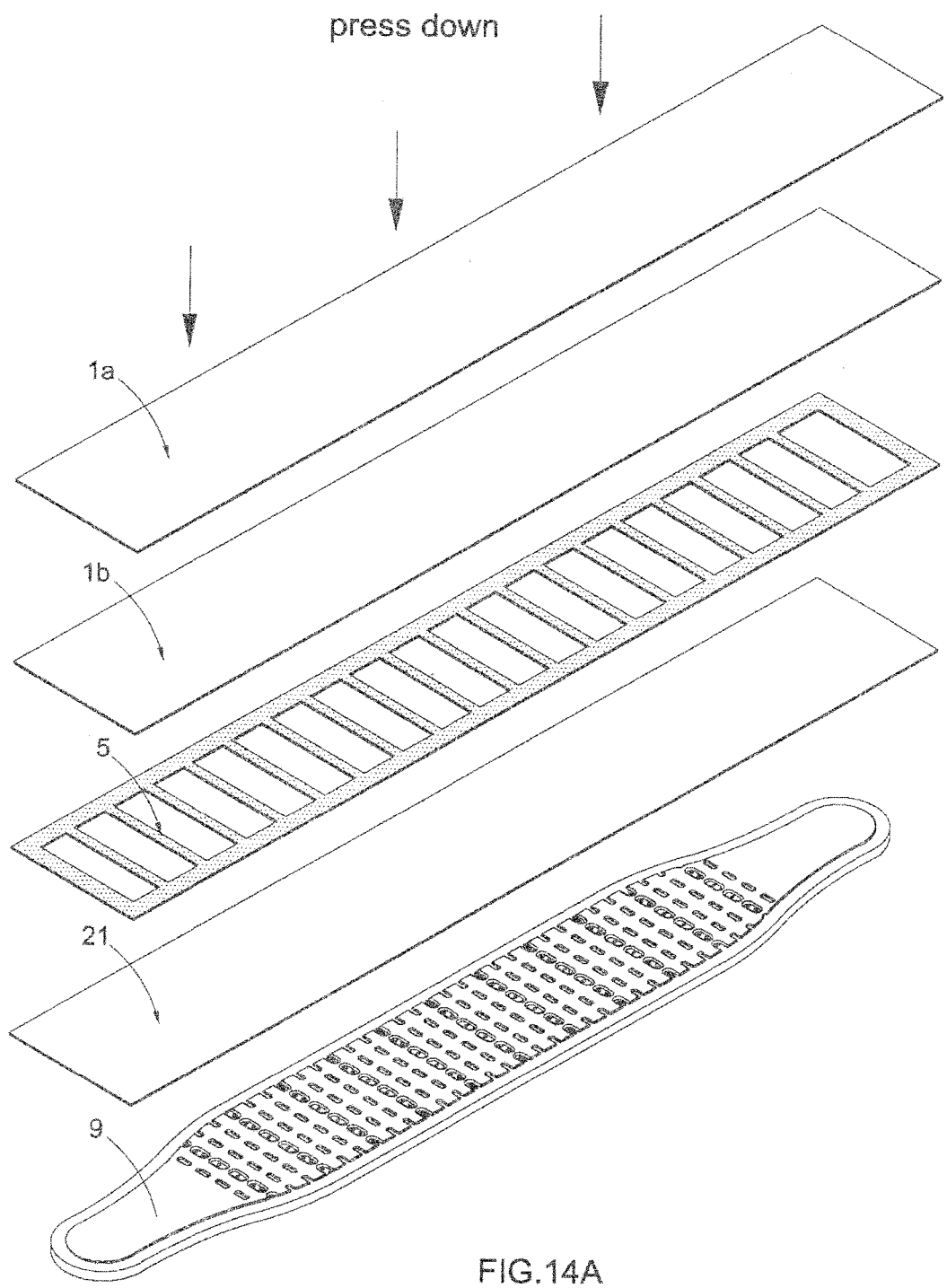
FIG. 14A is a perspective view illustrating the pressing procedure with a protection layer according to another preferred embodiment of the present invention.

In another preferred embodiment of the present invention, the first layer 1*a*, the second layer 1*b* and the shrinking layer 2 are bonded together as illustrated in FIG. 14A with a protection layer 5 for protecting the third layer 21 of the shrinking layer 2 from being bonded to the second layer 1*b* and the first layer 1*a*. The protection layer 5 is disposed between the shrinking layer 2 and the second layer 1*b* and has a pre-determined pattern to cover corresponding portions of the third layer 21.

The third layer 21 of the shrinking layer 2, the protection layer 5, the second layer 1*b* and the first layer 1*a* are provided onto the die 9 in turn, wherein the die 9 has pre-determined pattern disposed thereon. Then the first layer 1*a*, the second layer 1*b*, the protection layer 5 and the third layer 21 are pressed down to the die 9 with a pre-determined pressure. The pattern of the protection layer 5 is designed to cover part of the third layer 21 to resist the bonding to this part, and thereby a passage 23 for guiding an elastic band 22 to pass through is formed between the third layer 21 and the second layer 1*b*.

Figure 14B:
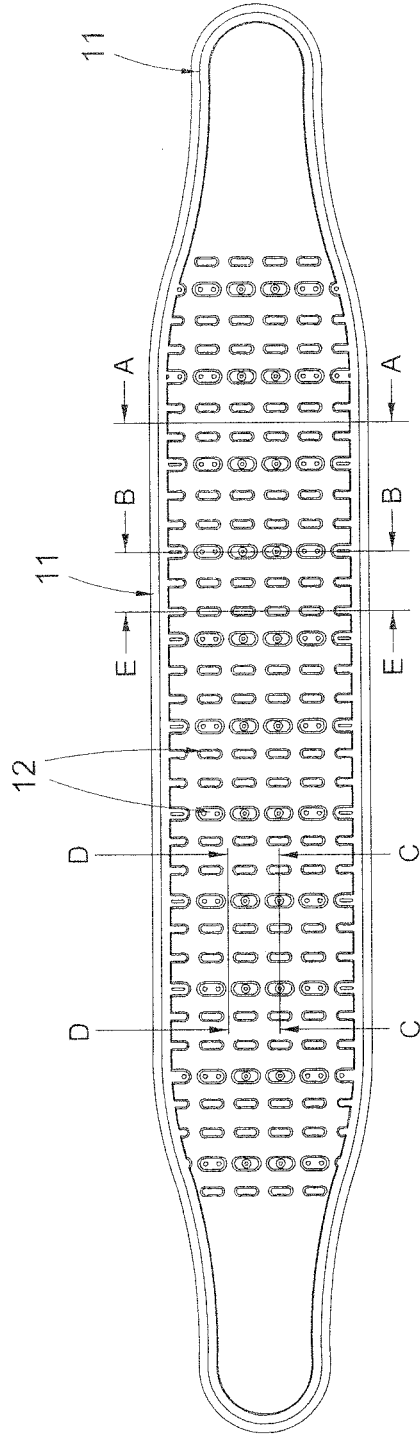
FIG. 14B is a perspective view of the product manufactured by the pressing procedure of FIG. 10A.

Referring to FIG. 14B, the first layer 1*a*, the second layer 1*b* and the third layer 21 are bonded together on the positions of the bonded regions 12, so that the air passages 4 are generated in the inner space 11 formed between the first layer 1*a* and the second layer 1*b* while a plurality of passages 23 are also generated between the second layer 1b and the third layer 21 for guiding the elastic bands 22 to drill through.

If not protected by the protection layer 5, the regions 12 on the third layer 21 will be bonded to the second layer 1b by being pressed to the die 9, but if protected by the protection layer 5, the regions 12 will separate from the second layer 1b to form inner space therein. Hence, due to the protection layer 5 and its pre-determined pattern, part of the regions 12 of the third layer 21 are not bonded to the second layer 1b to form additional passages 23 as illustrated in FIG. 14B.

As mentioned above, the bond line 3 is formed in accordance to the pre-determined pattern of the die 9 to bond the first layer 1a, the second layer 1b and the third layer 21 together under the press and/or the heat of the die 9. That means the material of the second layer 1b and the material of the third layer 21 could be heat-sealed, heat-welded, and adhered and so on to be bonded together, and even to be integrated together. Hence, the protection layer 5 should be made of the material which could stop these kinds of heat-sealing, hear-welding, and adhering and so on.

Figure 15A:
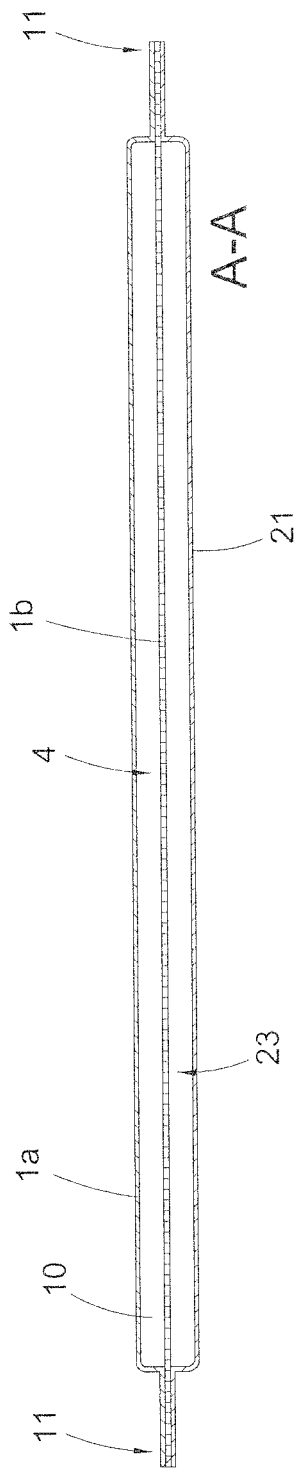
FIG. 15A is an A-A section view of the product of FIG. 14B.

Referring to FIG. 15A, the first layer 1a and the second layer 1b are bonded together on the outline 11 to form the inner space 10. An air passage 4 is generated in the inner space 10, while a passage 23 is generated between the second layer 1b and the third layer 21 to let the elastic band 22 pass through.

Referring to FIG. 15B, the first layer 1a, the second layer 1b and the third layer are bonded together not only on the outline 11, but also on the regions 12. The air passages 4 are generated in the inner space 10 formed between the first layer 1a and the second layer 1b.

Referring to FIG. 15E, the first layer 1a and the second layer 1b are bonded together not only on the outline 11, but also on the regions 12. However, these regions 12 of the third layer 21 are protected by the protection layer 5 from being bonded to the second layer 1b, thereby that an additional passage 23 is formed on these regions 12, which would be boned together if there is no protection layer 5.

Referring to FIG. 15C, the first layer 1a, the second layer 1b and the third layer 21 are bonded together on the regions 12 to form the air passages 4 in the inner space 10 between the first layer 1a and the second layer 1b and to form the passages 23 between the second layer 1b and the third layer 21 to let the elastic bands 22 pass through. As the additional passage 23 is formed by non-bonding of the regions 12, which actually separate the nearby passages 23, the additional passage 23 actually integrates with two nearby passages 23 to form a wide passage 230, which could permit at least two elastic bands 22 or a wide elastic band 220 to pass through.

Referring to FIG. 15D, some portions of the first layer 1a, the second layer 1b and the third layer 21 are not bonded together. Hence, the inner space 10 between the first layer 1a and the second layer 1b forms an air passage 4 here, which communicates with the air passages 4 shown in FIGS. 15A and 15B.

Figure 16B:
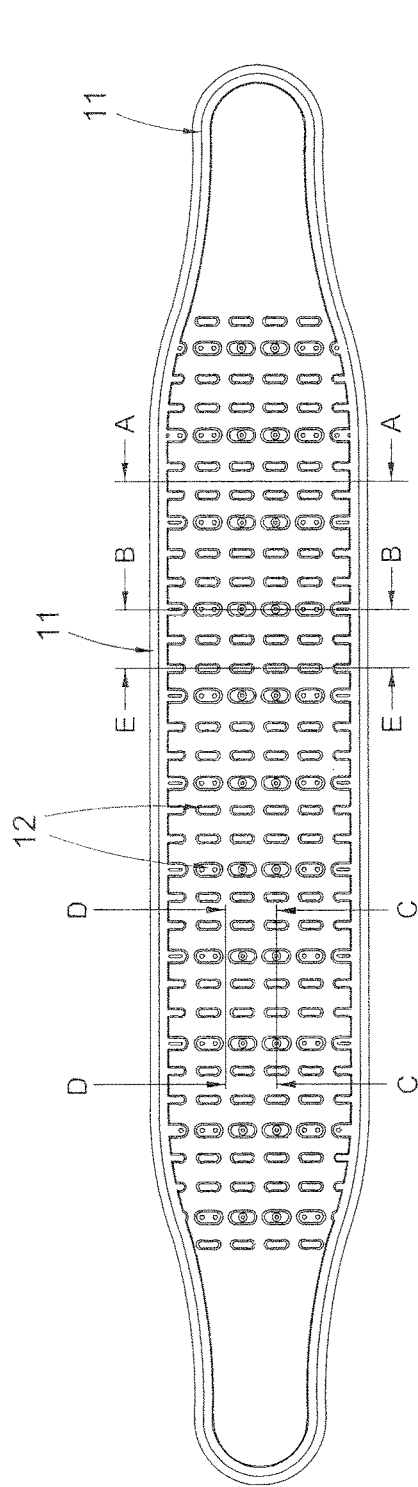
FIG. 16B is a perspective view illustrating the product manufactured by the procedure of FIG. 16A.

The elastic band 22 is guided to pass through the passage 23 and/or the additional passage 23 formed between the second layer 1b and the third layer 2 in the stretching state as illustrated in FIG. 16A. As mentioned above, the additional passage 23 actually integrates with two nearby passages 23 to form a wide passage 230, a wide elastic band 220 could be guided to pass through, as illustrated in FIGS. 16A and 16B.

Referring to FIG. 16B, the elastic band 22 is stretched and guided to extend on the outer surface of the second layer 1b and to pass through the passage 23 formed between the second layer 1b and the third layer 21.

Figure 17A:
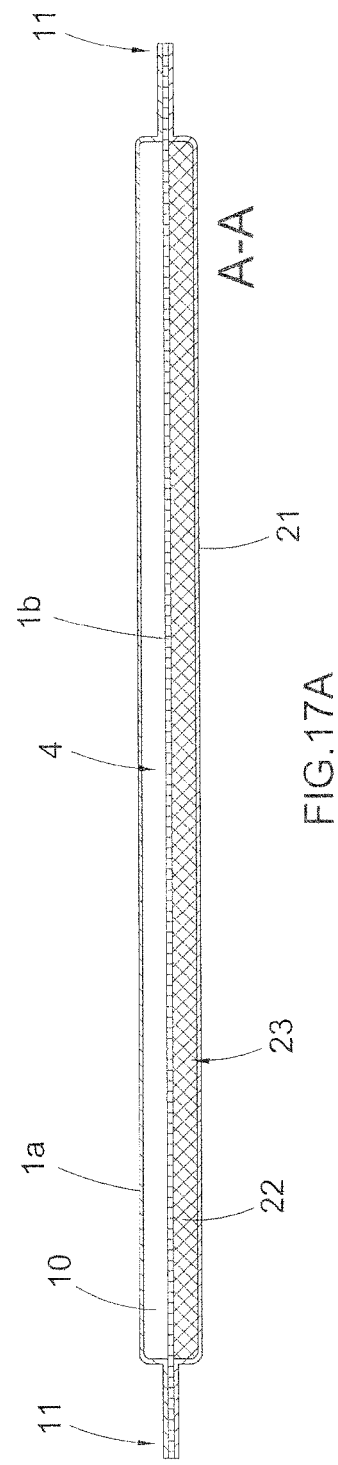
FIG. 17A is an A-A section view of the product of FIG. 16B.

Referring to FIG. 17A, an elastic band 22 has been guided to pass through the passage 23 formed between the second layer 1b and the third layer 21. The elastic band 22 is disposed on the outer surface of the second layer 1b and on the air passage 4 formed between the first layer 1a and the second layer 1b.

Referring to FIG. 17B, as the first layer 1a, the second layer 1b and the third layer are bonded together not only on the outline 11, but also on the regions 12, only the air passages 4 are formed, while no passage 23 is formed between the second layer 1b and the third layer 21. Hence, no elastic band 22 is disposed here.

Referring to FIG. 17E, which is different from FIG. 17B, the regions 12 of the third layer 21 are protected by the protection layer 5 from being bonded to the second layer 1b, thereby that an additional passage 23 is formed here and has an elastic band drilled through.

Referring to FIG. 17C and FIG. 17D, as the first layer 1a, the second layer 1b and the third layer 21 are bonded together on the regions 12, not only air passages 4 are formed in the inner space 10 between the first layer 1a and the second layer 1b, but also the passages 23 are formed between the second layer 1b and the third layer 21. Hence, the elastic bands 22 can be guided to pass through these passages 23 in the stretching state. Furthermore, as mentioned above, the additional passage 23 and two nearby passages 23 could compose a wide passage 230, which could permit a wide elastic band 20 pass through. Hence, the expansion band illustrated in FIGS. 17C and 17D has a plurality of passages 23 with elastic bands 22 disposed therein and at least one wide passage 230 with wide elastic band 220 disposed therein.

In this embodiment, as the wide elastic band 220 has big strain force than the elastic band 22, the wide passage 230 and the wide elastic band 220 could be used to partially enhance the shrinking of the shrinking layer 2. If a portion of the expansion band is shrunk more, when expansion band is filled with air, this portion will expand more than the other portion, which means this portion will provide more expansive force. Hence, expansion band has partially enhanced expansive force. Hence, the protection layer 5 could be designed with a pattern to form the wide passage 230 on special position of the expansion band. And that will further made the expansion band could provide enhanced expansive force on special position according to the requirement.

Referring to FIGS. 18A and 18B, a plurality of cuts 61 could be disposed on the outlines 11 of the expansion band with a pre-determined certain distance. When sewing along the outline 11 of the expansion band with a sleeve 62, two edges of each cut 61 will be sewed together to reduce the perimeter of the expansion band. This will balance the elastic deformation of the expanded expansion band to make the expansion band fit the human body better.

Figure 19:
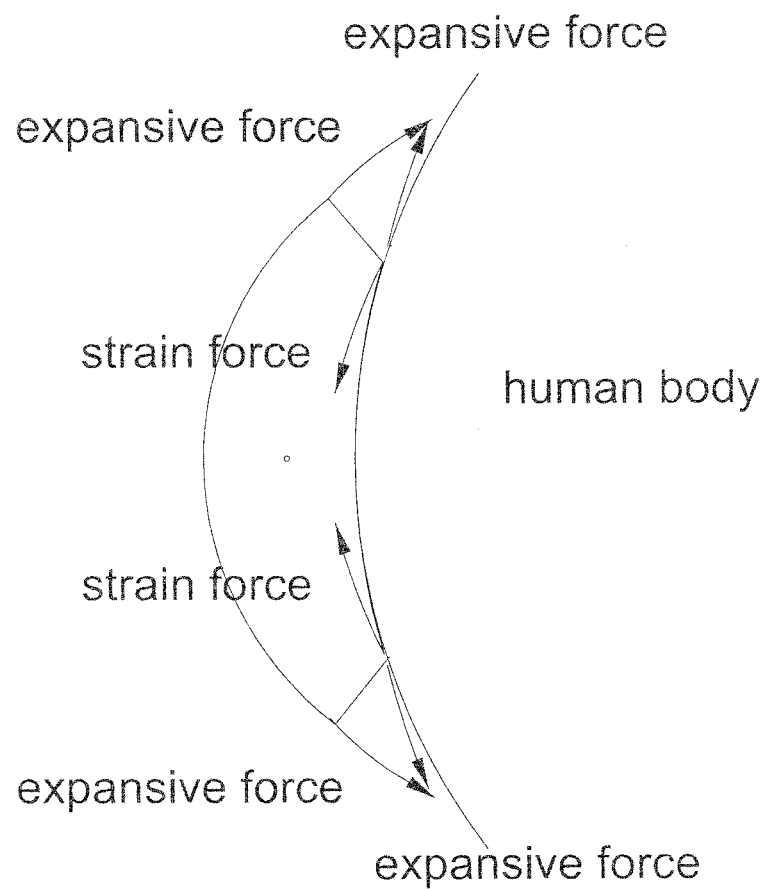
FIG. 19 illustrates the force distribution of the expansion band of FIG. 4.

Referring to FIG. 19, as the shrinking layer 2 is disposed on single side of the expansion band, the expansion band will be strained unilaterally by the shrinking layer 2, which means the expansion band will bear a unilateral strain of the shrinking layer 2. Hence, the expansive force on the side with shrinking layer 2 will be balanced by the unilateral strain force, resulting that the expansive deformation on the side with shrinking layer 2 is less than that on the other side. This will further make the expansion band fit the human body by surrounding the human body by the expansion band with the shrinking layer 2 attached to the human body.

Furthermore, when the side with shrinking layer 2 attaches to a human body, the side will directly provide an expansive force to the human body. As the other side has a bigger expansive deformation, its two ends will provide part of the expansive force on this side to the human body. Hence, the effective expansive force provided to the human body is actually increased and enhanced.

As the elastic bands 22 of the shrinking layer 2 are sewed to the first layer 1a and the second layer 1b instead of being adhered to the first layer 1a and the second layer, the strain force of the stretched elastic bands 22 will not directly effect on the bonded outline, the first layer 1a and the second layer 1b are bonded strong enough to avoid from being broken by the strain force of the elastic bands 22.

One skilled in the art will understand that the embodiment of the present invention as shown in the drawings and described above is exemplary only and not intended to be limiting.

It will thus be seen that the objects of the present invention have been fully and effectively accomplished. It embodiments have been shown and described for the purposes of illustrating the functional and structural principles of the present invention and is subject to change without departure from such principles. Therefore, this invention includes all modifications encompassed within the spirit and scope of the following claims.

What is claimed is:

1. An expansion band, comprising:
   first, second, and third layers, wherein said first layer, second layer, and said third layer are bonded together to form a bond line, wherein outlines of said first and second layers are sealed by said bond line to form an inner space between said first and second layers, wherein said bond line seals said outlines of said first and second layer to form said inner space and bonds regions of said first and second layers to divide said inner space into a plurality of air passages which communicate with each other; and
   a plurality of elastic bands extended between said second layer and said third layer.

2. The expansion band, as recited in claim 1, wherein said bond line bonds regions of said second and third layers to form a plurality of passages that said elastic bands are guided to pass through said passages respectively.

3. The expansion band, as recited in claim 2, wherein each of said elastic bands is stretched in a stretching state and is fixed to said third layer.

4. The expansion band as recited in claim 3, wherein said elastic bands parallel extends on said second layer in a width direction thereof.

5. The expansion band as recited in claim 4, wherein two ends of each of said elastic band are fixed to said outline on two opposed sides of said second layer in a stretching state respectively, such that said elastic band strains said first and second layers along a width direction to shrink said first and second layers.

6. The expansion band, as recited in claim 5, wherein said elastic bands are spacedly affixed to said third layer to form a shrinking layer.

7. The expansion band, as recited in claim 6, further comprising an air nozzle which communicates with said air passages.

8. The expansion band, as recited in claim 2, further comprising a protection layer disposed between said second and third layers, wherein said protection layer has a predetermined pattern to cover corresponding portions of said third layer for resisting said bonding between said second and third layers so as to enable said elastic bands to pass between said second and third layers.

9. The expansion band, as recited in claim 8, wherein said passages are defined at said portions of said third layer not being coupled to said second layer.

10. The expansion band, as recited in claim 9, wherein each of said elastic bands is stretched in a stretching state and is fixed to said third layer.

11. The expansion band as recited in claim 10, wherein said elastic bands parallel extends on said second layer in a width direction thereof.

12. The expansion band as recited in claim 11, wherein two ends of each of said elastic band are fixed to said outline on two opposed sides of said second layer in a stretching state respectively, such that said elastic band strains said first and second layers along a width direction to shrink said first and second layers.

13. The expansion band, as recited in claim 12, further comprising an air nozzle which communicates with said air passages.

14. The expansion band, as recited in claim 1, wherein each of said elastic bands is stretched in a stretching state and is fixed to said third layer.

15. The expansion band as recited in claim 1, wherein said elastic bands parallel extends on said second layer in a width direction thereof.

16. The expansion band as recited in claim 1, wherein two ends of each of said elastic band are fixed to said outline on two opposed sides of said second layer in a stretching state respectively, such that said elastic band strains said first and second layers along a width direction to shrink said first and second layers.

17. The expansion band, as recited in claim 1, wherein said elastic bands are spacedly affixed to said third layer to form a shrinking layer.

18. The expansion band, as recited in claim 1, further comprising an air nozzle which communicates with said air passages.

19. The expansion band, as recited in claim 1, further comprising a protection layer disposed between said second and third layers, wherein said protection layer has a predetermined pattern to cover corresponding portions of said third layer for resisting said bonding between said second and third layers so as to enable said elastic bands to pass between said second and third layers.

20. The expansion band as recited in claim 19, wherein two ends of each of said elastic band are fixed to said outline on two opposed sides of said second layer in a stretching state respectively, such that said elastic band strains said first and second layers along a width direction to shrink said first and second layers.

* * * * *